United States Patent
Bailey et al.

(10) Patent No.: US 11,912,785 B2
(45) Date of Patent: Feb. 27, 2024

(54) PEPTIDE COMPOSITIONS FOR SLOWING DEGRADATION OF VITAMIN MINERAL SUPPLEMENTS, FOODS, PHARMACEUTICAL AND COSMETICS

(71) Applicants: Steven W. Bailey, Mobile, AL (US); June E. Ayling, Mobile, AL (US)

(72) Inventors: Steven W. Bailey, Mobile, AL (US); June E. Ayling, Mobile, AL (US)

( * ) Notice: Subject to any disclaimer, the term of this patent is extended or adjusted under 35 U.S.C. 154(b) by 90 days.

(21) Appl. No.: 16/770,847

(22) PCT Filed: Dec. 6, 2018

(86) PCT No.: PCT/US2018/000390
§ 371 (c)(1),
(2) Date: Jun. 8, 2020

(87) PCT Pub. No.: WO2019/112630
PCT Pub. Date: Jun. 13, 2019

(65) Prior Publication Data
US 2020/0392180 A1 Dec. 17, 2020

Related U.S. Application Data

(60) Provisional application No. 62/708,364, filed on Dec. 6, 2017.

(51) Int. Cl.
| C07K 5/075 | (2006.01) |
| A23L 33/18 | (2016.01) |
| A23L 33/16 | (2016.01) |
| A23L 33/15 | (2016.01) |
| A61K 8/64 | (2006.01) |
| A61K 9/20 | (2006.01) |
| A61Q 5/02 | (2006.01) |

(Continued)

(52) U.S. Cl.
CPC ............ *C07K 5/0613* (2013.01); *A23L 33/15* (2016.08); *A23L 33/16* (2016.08); *A23L 33/18* (2016.08); *A61K 8/64* (2013.01); *A61K 9/2063* (2013.01); *A61Q 5/02* (2013.01); *A61Q 5/12* (2013.01); *C07K 5/0819* (2013.01); *C07K 5/1021* (2013.01); *A23V 2002/00* (2013.01); *A61K 2800/52* (2013.01)

(58) Field of Classification Search
CPC .. C07K 5/0808; C07K 5/0806; C07K 5/0819; C07K 5/0815; C07K 5/1021; C07K 5/06113; C07K 5/1019; C07K 5/0613; C07K 5/0812; C07K 5/1008; A61K 38/06; A61K 35/02; A61K 31/51; A61K 38/05; A61K 8/19; A61K 38/08; A61K 31/375; A61K 9/2063; A61K 38/07; A61K 8/64; A61K 33/34; A61K 33/26; A61K 9/2054; A61K 38/02; A61K 9/141; A61K 45/06; A61K 31/519; A61K 2300/00; A61K 2800/10; A61K 2800/52; A61K 33/15; A23L 33/18; A23L 33/16; A23L 33/15; A61Q 5/02; A61Q 19/00; A61Q 5/12; A23V 2200/00; A23V 2250/156; A23V 2250/1578; A23V 2250/1586; A23V 2250/1592; A23V 2250/161; A23V 2250/1626; A23V 2250/1642; A23V 2250/2108; A23V 2250/211; A23V 2250/2126; A23V 2250/55; A23V 2250/704; A23V 2250/708

See application file for complete search history.

(56) References Cited

U.S. PATENT DOCUMENTS

| 4,171,299 A | 10/1979 | Hamburger |
| 4,863,898 A * | 9/1989 | Ashmead ................ A61P 43/00 514/502 |

(Continued)

FOREIGN PATENT DOCUMENTS

| CN | 104 177 477 | 12/2014 |
| EP | 2266590 | 12/2010 |

(Continued)

OTHER PUBLICATIONS

Weinreb; Neuroprotective multifunctional iron chelators from redox-sensitive process to novel therapeutic opportunities; Antioxidants & Redox Signaling 13.6; Sep. 15, 2020; 919(31).
Thomas, S.; International Search Report and Written Opinion; PCT/US2018/000390; dated Jan. 29, 2019.
Stocker A. et al. "Trace and mineral elements in royal jelly and homeostatic effects" Journal of Trace Elements in Medicine and Biology, vol. 19, No. 2-3, Dec. 2, 2005, pp. 183-189.

(Continued)

*Primary Examiner* — Doan T Phan
(74) *Attorney, Agent, or Firm* — Casimir Jones, S.C.; Robert A. Goetz

(57) ABSTRACT

Compositions of foods, vitamin and mineral supplements, topical or oral drugs, and cosmetic products containing a small peptide or peptides for slowing degradation, for example by transition metals. The peptides are di, tri, terra-, and/or penta-peptides containing two or more aspartic acid residues. The degradation of several of the vitamin and other constituents vitamin-mineral supplements can be considerably slowed by composition incorporating such peptides, particularly if soluble (and thus bioavailable) forms of copper and/or iron are also present. The peptides can be hydrolyzed by the normal digestive process thus releasing bound metals. Multiple aspartate peptide(s) compositions with foods, topical or oral drugs, cosmetic, and hair care products can replace synthetic chelating preservative agents. Methods are also described to effectively slow degradation and preserve the above products using multiple aspartate peptides.

20 Claims, 6 Drawing Sheets
Specification includes a Sequence Listing.

(51) Int. Cl.
*A61Q 5/12* (2006.01)
*C07K 5/093* (2006.01)
*C07K 5/113* (2006.01)

(56) References Cited

U.S. PATENT DOCUMENTS

| | | |
|---|---|---|
| 6,426,424 B1 | 7/2002 | Ashmead et al. |
| 2002/0110632 A1 | 8/2002 | Nunes et al. |
| 2003/0129194 A1 | 7/2003 | Mazes |
| 2003/0206969 A1 | 11/2003 | Nidamarty et al. |
| 2004/0063628 A1* | 4/2004 | Piccariello ............. A61K 47/62 |
| | | 514/21.8 |
| 2004/0180102 A1 | 9/2004 | Patt |
| 2006/0013892 A1 | 1/2006 | Ashmead |
| 2008/0096804 A1 | 4/2008 | Miroshnychenko |
| 2010/0093850 A1 | 4/2010 | Park |
| 2010/0215768 A1 | 8/2010 | Pero et al. |
| 2011/0027209 A1 | 2/2011 | Anzali |
| 2017/0188618 A1* | 7/2017 | Ulijn .................... A23L 33/175 |

FOREIGN PATENT DOCUMENTS

| | | |
|---|---|---|
| GB | 1539102 | 1/1979 |
| JP | 2007 217358 | 8/2007 |
| WO | 9950286 | 4/2009 |
| WO | 2010037553 | 4/2010 |

OTHER PUBLICATIONS

EP Search Report, EP Patent Application No. 18886714.7, dated Oct. 25, 2021, 4 pages.

\* cited by examiner

PEPTIDE COMPOSITIONS FOR SLOWING DEGRADATION OF VITAMIN MINERAL SUPPLEMENTS, FOODS, PHARMACEUTICAL AND COSMETICS

CROSS-REFERENCE TO RELATED APPLICATIONS

This application is a national stage under 35 U.S.C. 371 of International Application No. PCT/US2018/000390 (currently published), filed Dec. 6, 2018. International Application No. PCT/US2018/000390 cites the priority of U.S. Provisional Application No. 62/708,364, filed Dec. 6, 2017.

SEQUENCE LISTING

The text of the computer readable sequence listing filed herewith, titled "40848-252_SQL_ST25", created Sep. 25, 2023, having a file size of 2,848 bytes, is hereby incorporated by reference in its entirety.

FIELD

The present technology is related to peptide compositions for slowing the degradation of vitamin-mineral supplements, foods, pharmaceuticals, and cosmetics, as well as methods of making and using such compositions. The present peptide compositions include short two to five residue peptides having at least two aspartic acid residues.

BACKGROUND

Deficiencies in mineral nutrients are a major contributor to world-wide burden of poor health. Consumption of mineral supplements can be a large contributor to intake, especially in the Western diet. Essential trace minerals are often combined with single vitamins or in multivitamin-mineral preparations. Among these minerals are several that are transition metals having multiple oxidation states such as iron, copper, chromium, and manganese. It has been recognized for many decades that such metals are capable of degrading various vitamins and other nutrients. For example, the presence of copper has been shown to increase the rate of vitamin B12 degradation [Kondo, H et al, J Clin Invest. 1982 70(4):889-98.]. Several transition metals, such as iron and copper, are well known to catalyze the oxidation of ascorbic acid [Vitamin C in Health and Disease (1997) pp. 59-94. Packer, L., Fuchs, J. (Eds.). Marcel Dekker New York; L. D. Muller J. Pharm. Biomed. Anal., 25 (2001), p. 985]. The presence of iron and ascorbic acid has been shown to generate hydroxyl radicals in baby food [Almaas, R et al, European Journal of Pediatrics Volume 156, Issue 6, 1997, Pages 488-492]. Moreover, the combination of iron and ascorbic acid has been reported to induce gastric ulcers in rats [Naito Y, et al, Digestion. 1995; 56(6):472-8].

The problem of oxidative degradation in supplements is exacerbated by the use of soluble forms of copper such as the sulfate salt or amino acid chelates. The catalytic action of copper can be decreased (but not eliminated) by the use of the highly insoluble cupric oxide. However, numerous studies have shown that cupric oxide has extremely low bioavailability [Baker D H. Cupric oxide should not be used as a copper supplement for either animals or humans. J Nutr. 1999 129(12):2278-9]. Although many multivitamin-mineral supplements are formulated with cupric oxide, this does not provide the copper needed by humans or animals. It is apparent that manufacturers include this ineffective form in order to avoid the destruction of the other product components as demonstrated above.

Despite the considerable problems associated with directly combining iron and/or copper with other sensitive micronutrients, such as vitamins, there is currently no technology to alleviate the degradation that occurs not only within the product during storage, but also after consumption or during dissolution testing (which is often designed to simulate consumption).

Many foods, topical or oral drugs, and cosmetics are stabilized against degradation by inclusion of EDTA (ethylenediamine tetraacetic acid). EDTA inhibits rancidity (disagreeable odor or taste of decomposing oils or fats) in salad dressings, mayonnaise, sauces, and other foods. It also promotes color retention. This chelating agent has a very high affinity for many metals, and is considered to be safe for use in certain foods within concentration ranges specified by the FDA and other national regulatory agencies. It is also used in topical or oral drugs, and cosmetics. EDTA also has antimicrobial and antibiofilm activities. Moreover, it potentiates other antimicrobials for example those used in wound care. However, although about 5% of oral intake is absorbed, it is not metabolized by the body, and administration of high levels of EDTA can lead to reduced blood calcium and increased urine calcium. Moreover, it is a persistent environmental pollutant, especially if complexed to metal. Non-biodegradable chelating agents such as EDTA also increase the difficulty of metal removal from waste streams.

SUMMARY

Small peptides containing two or more aspartic acid residues (multiple aspartate peptides) been discovered that slow the degradation of vitamins and other nutrients, especially in vitamin-mineral supplements, of foods, topical or oral drugs, and of cosmetics. The peptide or peptides can be premixed with metal or metals as salts, or added to the final product separately from the metals, or both. An advantage of small peptides over traditional chelators (for example, EDTA) is that the small peptides can be hydrolyzed by digestive proteases, thus releasing the metal(s) for subsequent absorption. Moreover, unlike EDTA, these peptides are biodegradable.

Degradation can be slowed by a composition comprising an effective amount of one or more peptides or a pharmaceutically acceptable salt thereof, wherein each peptide has two to five amino acid residues and at least two of the residues are aspartic acid residues; one or more physiologically acceptable minerals or other physiologically acceptable agents capable of degrading one or more nutrients or drugs; and one or more nutrients and/or drugs sensitive to degradation by the physiologically acceptable minerals or other physiologically acceptable agents; wherein the one or more peptides preferably do not contain histidine.

A composition comprising an effective amount of one or more peptides or a pharmaceutically acceptable salt thereof, wherein each peptide has two to five amino acid residues and at least two of the residues are aspartic acid residues; one or more physiologically acceptable minerals comprising at least copper and/or iron; and one or more nutrients and/or drugs sensitive to degradation by the copper and/or iron; wherein the one or more peptides preferably do not contain histidine is preferred.

A composition comprising an effective amount of one or more peptides or a pharmaceutically acceptable salt thereof, wherein each peptide has two to five amino acid residues and at least two of the residues are aspartic acid residues; one or more minerals; one or more nutrients and/or drugs sensitive to degradation or color change by said one or more physiologically acceptable minerals; wherein the effective amount of peptide is sufficient to decrease the rate of degradation of the one or more nutrients and/or of color change and/or drugs by at least 5% is also preferred.

An example of a method for decreasing the rate of decomposition of nutrients in vitamin-mineral products and/or drug products during ingestion and/or dissolution testing comprises incorporation of an effective amount of one or more peptides or a pharmaceutically acceptable salt thereof, wherein each peptide has two to five amino acid residues and at least two of the residues are aspartic acid residues; wherein the one or more peptides preferably do not contain histidine.

An example of a cosmetic or hair-care product composition comprises a topical carrier and the an effective amount of one or more peptides or a pharmaceutically acceptable salt thereof, wherein each peptide has two to five amino acid residues and at least two of the residues are aspartic acid residues; wherein the one or more peptides preferably do not contain histidine.

DETAILED DESCRIPTION

Figure 1:
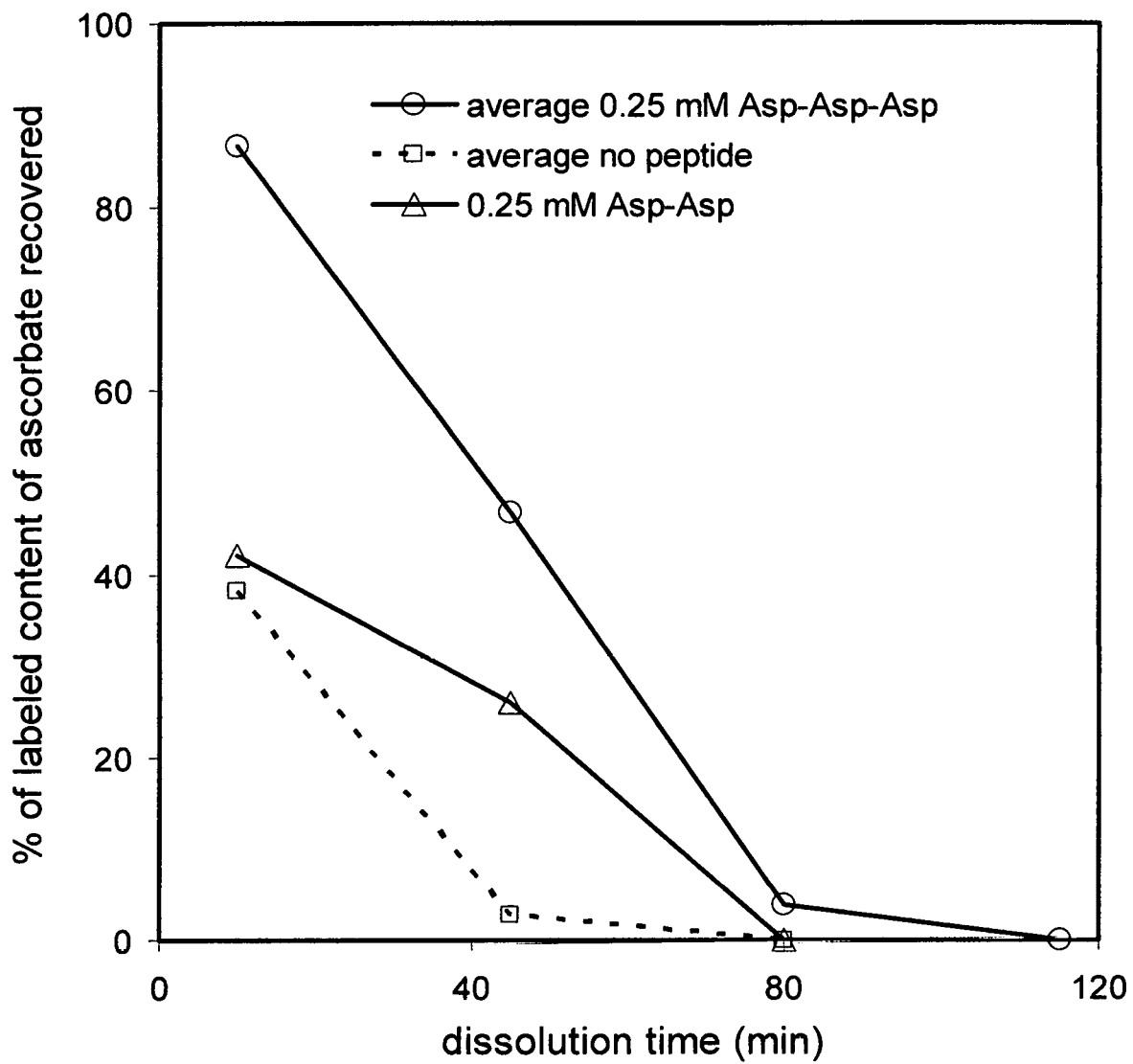
FIG. 1 shows the amount of ascorbate recovered (expressed as a percentage of the labeled content) from USP type 2 dissolution experiment containing a commercially available multivitamin-mineral supplement (1a) in the absence and presence of 0.25 mM Asp-Asp or Asp-Asp-Asp over time.

The compositions of the present technology are a food, a vitamin and mineral supplement, a topical drug, an oral drug, a cosmetic, or hair care product and one or more multiple aspartate peptide(s), wherein said peptide is present in an amount capable of slowing degradation of said food, a vitamin-mineral supplement, topical drug, oral drug, cosmetic, or hair care product. Di-, tri, tetra and penta-peptides are preferred. Additional acidic residues in these multiple aspartic acid peptides are such as glutamic acid, sulfonated amino acids, phosphorylated amino acids, and gamma-carboxy-glutamate can also increase effectiveness. Examples of multiple aspartate peptides are, but are not limited to, diaspartic acid, and tripeptides, tetrapeptides, and pentapeptides that contain at least two residues of aspartic acid. Mixtures of different peptides are also useful such as those having different sequences. It is preferred that at least one of the peptides in such a mixture contain at least two aspartic acid residues. Multiple aspartate peptides can be predominately of one chain length, or mixtures of different lengths. One example is a mixture of diaspartic acid, triaspartic acid, tetraaspartic acid, and pentaaspartic acid. For such mixture it is preferred that the most abundant form be triaspartic acid. The compositions and methods described herein are suitable for both human and animal use, where the latter includes, among others, cats, dogs, cows, sheep, pigs, and poultry. In the present disclosure, the phrases "diaspartic acid," "triaspartic acid," "tetraaspartic acid" and "pentaaspartic acid" or salts thereof (such as calcium diaspartate) refer to peptide sequences of aspartic acid, e.g. Asp-Asp, Asp-Asp-Asp, Asp-Asp-Asp-Asp [SEQ ID NO: 1], Asp-Asp-Asp-Asp-Asp [SEQ ID NO: 2], and calcium Asp-Asp, respectively. They do not refer to separate (non-covalently linked) amino acids. For example, in the present disclosure, calcium diaspartate does not signify a salt of calcium containing two separate (non-covalently bound) aspartic acid molecules (CAS: 39162-75-9) that are not linked together into a peptide.

For multiple aspartate peptides having more than two amino acids, those which are not aspartic acid can be any of the amino acids found in proteins, for example, glutamic acid, (which is especially preferred), glycine, alanine, valine, leucine, isoleucine, serine, cysteine, selenocysteine, threonine, methionine, proline, phenylalanine, tyrosine, tryptophan, lysine, arginine, asparagine, and glutamine, but preferably not unmodified histidine. Post-translationally or otherwise naturally modified amino acids can also be used. Many such modifications are known to the art. Examples that can be used with the methods and compositions described herein include, but are not limited to, phosphorylated amino acids (e.g., phosphoserine, phosphothreonine, phosphotyrosine, phosphoaspartic acid, phosphoglutamic acid, phosphohistidine, phosphocysteine, etc.), gamma-carboxy-glutamate, pyrrolysine, selenocysteine, hydroxylated amino acids (e.g., asparagine, aspartic acid, proline, lysine, etc.), alkylated amino acids (e.g., methylated forms of histidine, lysine, glutamic acid, etc.), sulfonated amino acid (e.g., serine, threonine, tyrosine, etc.), citrulline, N- and O-glycosylated amino acids. For peptides containing only aspartyl residues, triaspartic acid is preferred, although tetraaspartic acid is just as effective on a molar basis. Tetraaspartic acid has a higher molecular weight and potentially requires additional synthetic steps than triaspartic acid. Ala-Asp-Asp was found to be about half as effective on a molar basis as triaspartic acid, although its lower molecular weight makes up for some of this difference on a per weight basis. Examples are Asp-Asp-Glu, Asp-Glu-Asp, Glu-Asp-Asp, Asp-Asp-Ala, Asp-Asp-Glu, Asp-Asp-Asp-Glu [SEQ ID NO: 3], Asp-Asp-Ala, Ala-Asp-Asp-Asp [SEQ ID NO: 4], Gly-Asp-Asp, Asp-Asp-Cys, Asp-Asp-Met and others some of which are listed in Table 1.

TABLE 1

| | |
|---|---|
| Asp-Asp | Asp-Asp-Cys |
| Asp-Asp-Glu | Asp-Asp-Met |

TABLE 1-continued

| | |
|---|---|
| Asp-Glu-Asp | Arg-Asp-Asp |
| Glu-Asp-Asp | Lys-Asp-Asp |
| Asp-Asp-Ala | Asp-Asp-Asp-Asp [SEQ ID NO: 1] |
| Asp-Asp-Glu | Asp-Asp-Asp-β-Asp [SEQ ID NO: 14] |
| Asp-Asp-Ala | Asp-Asp-Asp-Glu [SEQ ID NO: 3] |
| Gly-Asp-Asp | Gly-Asp-Asp-Asp [SEQ ID NO: 5] |
| Ala-Asp-Asp | Arg-Asp-Asp-Asp [SEQ ID NO: 6] |
| Val-Asp-Asp | Lys-Asp-Asp-Asp [SEQ ID NO: 7] |
| Leu-Asp-Asp | Arg-Asp-Asp-Arg [SEQ ID NO: 8] |
| Phe-Asp-Asp | Arg-Asp-Asp-Lys [SEQ ID NO: 9] |
| Tyr-Asp-Asp | Arg-Asp-Asp-Asn [SEQ ID NO: 10] |
| Asp-Asp-Try | Arg-Asp-Asp-Phe [SEQ ID NO: 11] |
| Asp-Asp-Phe | Arg-Asp-Asp-Leu [SEQ ID NO: 12] |
| Ala-Asp-Asp | Arg-Asp-Asp-Val [SEQ ID NO: 13] |

While peptides containing residues that are fully or partially racemic (due to the nature of the starting materials or by racemization during synthesis) can be effective, it is preferred that the peptides be substantially chirally pure at each position in the sequence. By Asubstantially@, it is meant that chiral purity of the residue in each position be greater than 80%, or more preferably greater than 90%, and most preferably greater than 95%. The peptides can have some residues which are the substantially pure L-isomer, and contain other residues which are the substantially pure D-isomer. Peptides made of some or all residues that are predominately the unnatural D-isomers can also inhibit metal catalyzed oxidation reactions. Those made primarily of the natural amino acid L-isomers are capable of being proteolyzed in the digestive track, which thus liberates the bound metals to be more quickly absorbed into the blood than those containing D-isomers. Most animals including humans are exposed to some amount of D-amino acids (which can be detected in blood and urine). In particular, D-aspartic acid is biosynthesized in the human brain. Thus, the rate of proteolysis can be controlled by inclusion of a D-amino acid as part of the multiple aspartate peptide.

The degradation of vitamins, foods, topical or oral drugs, cosmetics, or hair is often due to the presence of transition metals. These can be explicitly added, such as in vitamin-mineral supplements. Compositions that are do not contain explicitly added transition metals whether a vitamin, food, a topical or oral drugs, or cosmetic can still benefit from increased stability by combination with peptides due to the presence of trace or unquantified metals. Moreover, hair itself often contains significant bound metal (such as copper or iron) that affect its properties.

Uptake of a metal from the intestinal tract can be influenced by the several factors controlled by the peptides to which it is bound. Moreover, clearance of peptides from the digestive tract can occur by several mechanisms. For example, the peptide can be proteolyzed into its amino acid constituents which will have lower affinity for the metal, allowing for its subsequent uptake into the enterocyte. Uptake of transition metals can enhance stability of the other sensitive nutrients still remaining in the intestinal tract. In addition, a considerable portion of the total intestinal uptake of amino acids occurs in the form of di- and tri-peptides, which are substrates for several peptide transporters as well as by a paracellular route. The use of a small peptide to quench the redox activity of the transition metals present in a food or supplement has the advantages over other chelating agents in being ultimately digestible and exposing the consumer only to natural products. The selection of the amino acids in the peptide which are not aspartic acid can, in part, be tailored to a give an optimal rate of proteolysis in the digestive tract. This, in turn, can modulate the release of the bound transition metals.

The sequence Asp-Asp-Asp (single letter code: DDD) is found naturally within many larger proteins in microbes and eukaryotes. For example, this is found in within lactalbumin, caspase 3, and coagulation factor VIII. The sequence Asp-Asp-Asp-Asp (DDDD) [SEQ ID NO: 1] has been found among the peptides contained in hydrolyzed beer yeast Thus, humans have long been exposed to similar peptides resulting from digestion of dietary protein indicating that they are safe for consumption. Large proteins in of themselves are, however, not efficient for use in vitamin preparations even if they both bound metal and hindered its redox reactions due to their much high molecular weights.

Although most peptide amide linkages are made through the alpha amino and carboxyl groups, peptides linked via the beta carboxyl group of aspartic acid, the gamma carboxyl group of glutamic acid, and/or the epsilon group of lysine can also be useful for controlling the redox activity of transition metals. Glutathione and folate polyglutamic acids illustrate some naturally occurring peptides with gamma-linkages. Peptides containing such linkages are still capable of being cleaved by proteases. Examples of a multiple aspartate peptides containing a beta-linkage are α-Asp-β-Asp, α-Asp-α-Asp-β-Asp, α-Asp-β-Asp-α-Asp, and α-Asp-β-Asp-X, where X is another amino acid as described above. The inclusion of a hydrophobic residue (for example, valine, leucine, isoleucine, methionine, or phenylalanine) can aid, among other things, the isolation and purification of the peptide after its synthesis. The ability of 1,1,1-triaspartic acid to inhibit oxidative destruction of other multivitamin components was found to be dependent on the presence of a free N-terminal amino group as determined by the lack of effectiveness of N-acetyl-1,1,1-triaspartic acid.

The ratio of metal, metals, and/or other cations such as choline to the multiple aspartate peptide, in vitamin-mineral or other nutritional product, topical or oral drug product, or cosmetic product can be variable. More relevant to effectiveness in preventing product degradation is the total amount of the multiple aspartate peptide or multiple aspartate peptides. For vitamin-mineral products the preferred range of peptide can be based on the mole amount in the product composition that minimized degradation both on the shelf and during digestion or dissolution testing. For food, topical or oral drugs, and cosmetic products minimization degradation during the shelf life is of particular importance.

An appropriate way of determining degradation during digestion, for example of vitamin-mineral compositions is through the use of dissolution methods, for example as set forth in the U.S. Pharmacopeia. As the amount of transition metals (for example, copper or iron) capable of promoting degradation (such as redox reactions) increases, the mole amount of peptide needed to achieve a particular level of stabilization can also increase. For example, with a vitamin-mineral product containing the U.S. Daily Value of a soluble form of copper (2 mg as the elemental weight, 31.5 micromole per serving size), useful amounts of, for example, triaspartic acid (as the total of all salt or acid forms) can be between about 0.01 millimoles to about 3 millimoles per serving size (for example, 0.01 mmole, 0.02 mmole, 0.03 mmole, 0.04 mmole, 0.05 mmole, 0.06 mmole, 0.07 mmole, 0.08 mmole, 0.09 mmole, 0.1 mmole, 0.15 mmole, 0.2 mmole, 0.25 mmole, 0.3 mmole, 0.4 mmole, 0.5 mmole, 0.6 mmole, 0.7 mmole, 0.8 mmole, 0.9 mmole, 1.0 mmole, 1.1 mmole, 1.2 mmole, 1.3 mmole, 1.4 mmole, 1.5 mmole, 1.6 mmole, 1.7 mmole, 1.8 mmole, 1.9 mmole, 2.0 mmoles, 2.25 mmoles, 2.5 mmoles, 2.75 mmoles, 3.0 mmoles per serving size). The serving size is that quantity of product indicated on the product label that when consumed per occasion delivers the labeled nutrients. A serving size for a vitamin mineral product, for example, might be one tablet or capsule, but also can be labeled as two or more tablets or capsules. In specifying a mole amount of a peptide mixture, the above range refers to the amount of each individual peptide. Other multiple aspartate peptides can require different total amount to achieve similar effectiveness (as can be judged, for example, by USP dissolution experiments). For example, the mole amount of Ala-Asp-Asp needed is about twice that of Asp-Asp-Asp to provide similar effectiveness. With a lower amount of added transition metal, e.g. copper, the total amount of added peptide can be lower to produce a desired level of product stability. It should, thus, be appreciated that an important factor is the total amount of the peptide or peptides in the composition, regardless of which salt or acid forms are added in relation to the amount of transition metals present. The amount of a peptide contained in a vitamin-mineral product for the purpose of slowing its degradation can be specified by the total moles of peptide in a serving size. This is more informative than specifying only its ratio to of any of the potentially several metals in the product. Moreover, the optimal amount depends on the particular constituents of the vitamin-mineral or other nutritional product since the presence of high concentrations of some metals can decrease the effectiveness by competition for binding of the peptide or peptides even if not promoting degradation in of themselves. The optimal amount can be determined by dissolution or other stability assays for each product formulation. The effective amount of a multiple aspartate peptide or peptides in a composition is that that which can slow the rate of degradation by at least than 5%, preferably at least 10%.

For food, topical or oral drug, and cosmetic compositions the amount of peptide is preferably given as the molar concentration. The difference between specifying the mole amount given for a vitamin-mineral supplement composition versus a molar concentration for the food, topical or oral drug, or cosmetic composition is due to the need for slowing the degradation of the former occurring after dissolution into a certain volume of either digestive juices or into a simulating test thereof. With food, topical or oral drug, and cosmetic compositions the degradation (such as oxidation, discoloration, development of rancidity, or by microbial contamination) is primarily desired to be slowed during storage, in which case the volume of the product is approximately known, and a concentration can be specified. While many of these products do not have transition metals added explicitly as an ingredient, they still contain such metals that are endogenous to, or are contaminants of the other ingredients. A hair care product can, in addition, protect the hair from copper, iron, or other metals already bound within the hair. For food, topical or oral drug, cosmetic and hair compositions this concentration can be between about 0.02 mM and about 6 mM (for example 0.02 mM, 0.03 mM, 0.04 mM, 0.05 mM, 0.06 mM, 0.07 mM, 0.08 mM, 0.09 mM, 0.1 mM, 0.15 mM, 0.2 mM, 0.25 mM, 0.3 mM, 0.4 mM, 0.5 mM, 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 2.25 mM, 3.50 mM, 3.75 mM, 4.0 mM, 4.25 mM, 4.50 mM, 4.75 mM, 5.0 mM, 5.25 mM, 5.50 mM, 5.75 mM, 6.0 mM) in the example of the peptide being triaspartic acid. For a product that is in a packing medium, for example canned beans, the volume used for calculating the added the multiple aspartate containing peptide is the combination of the product and the packing medium. The multiple aspartate peptide or peptides can conveniently be added first to the liquid packing medium, or to the combination of the medium with the product. For example, a product having a total (product plus medium) volume of 8 fluid ounces (237 mL) would contain between about 0.005 mmoles and 1.4 mmoles of, for example, triaspartic acid to achieve the above concentration range. A one ounce product would contain between about 0.6 micromoles and 177 micromoles. Due to the large variability of potential product weights for food, topical or oral drug, cosmetic or hair compositions, it is thus clear that a molar concentration is more meaningful than a mole amount (the latter being more appropriate for the above vitamin-mineral compositions. Multiple aspartate peptides other than triaspartic acid can require different molarities to achieve similar effectiveness in slowing degradation. For example, the concentration of diaspartic acid needed to achieve an effectives similar to triaspartic acid can be about twice those described above in this paragraph for triaspartic acid. In specifying a molar concentration of a peptide mixture, the above range refers to the concentration of each individual peptide. Peptides have several advantages over commonly used preservatives, such as EDTA (ethylenediamine tetraacetic acid). The peptides of this invention when taken orally are, unlike EDTA, digested to amino acids which can be utilized by the body=s normal metabolism. Moreover, even if not ingested, these can be broken down by natural processes, which is an advantage for products such as shampoos and conditioners that are largely washed into sewage systems.

For several of the products herein described the improvement in the stability of the components with increasing multiple aspartate peptide was discovered to follow a asymptotic curve. For example, for one particular product, the amount of tetrasodium 1,1,1-triaspartate in a USP type 2 dissolution experiment required to give half of the maximal stability of the ascorbic acid component of a particular multivitamin-mineral product was about 11.3 mg (0.025 mmoles peptide in a 0.5 L test volume). A greater level of stabilization can be achieved with a higher amount of peptide, but at the expense of increased product weight. It can be appreciated that since the total weight/size of a vitamin-mineral tablet or capsule, etc. is limited, it can be advantageous to have any counter-ion associated with the multiple aspartate peptide or peptides have more nutritional value than sodium (for example, potassium or magnesium), though sodium is effective. The free acid can be used preferably if appropriately neutralized during dissolution by the other product components.

The ability of multiple aspartate peptides to hinder oxidation is decreased in acidic conditions. Therefore, it is preferred that the pH of a vitamin-mineral product containing a multiple aspartate peptide should be above about pH 6 upon dissolution. Since the free acid form of the multiple aspartate peptides can contribute to the overall acidity, this can be converted to a more neutral salt form or forms. Alternatively, the presence of alkaline substances in the vitamin-mineral product, for example calcium carbonate or magnesium oxide, can be used to adjust the pH to be in the optimal range once dissolved. The copper present in a vitamin-mineral product can be added as a preformed salt with a multiple aspartate peptide, or formulations where the multiple aspartate peptide is added as a different salt form, or as a combination with other salt forms in addition to that with copper. Other salt forms of the multiple aspartate peptides include sodium, potassium, magnesium, and calcium, or any other metal to be added to the vitamin-mineral product. The magnesium or calcium salts are particularly useful since these often are present as a considerable percentage of the total weight of the final product. When the multiple aspartate peptide is used in substitution for the carbonate, citrate, fumarate, or other counter-ions often accompanying these metals, the extra weight due the peptide is offset by that which would otherwise be present. For example, including 52.5 mg of $Ca_{1.5}$-1,1,1-triaspartate (not counting any water of hydration) would provide 0.125 mmol of 1,1,1-triaspartate and 7.5 mg of elemental calcium. Had this amount of calcium instead been included in the form of its citrate salt, this would have added about 31 mg (not counting any water of hydration). In this case, product weight increases only about 21 mg per dose by the substitution of triaspartate for citrate.

Since as mentioned above, the effectiveness of multiple aspartate peptides is optimal above about pH 6, some dosage formulations can benefit from enteric coatings, or other strategies that as are well known in the industry, that delay dissolution until after any stomach acid has been neutralized by the digestive tract.

The metals in a vitamin-mineral product can be present either in a salt form well understood to the art of such products, or as metal-peptide complex, or both. For example, copper is typically present in products as cupric sulfate, cupric oxide, cupric citrate, cupric acetate, copper sebacate, cupric bis-glycinate and other amino acid chelates, and the like. Iron is typically present in products as ferric oxide, ferrous fumarate, ferrous sulfate, ferric phosphate, ferrous bisglycinate chelate, carbonyl iron, ferrous succinate, ferrous aspartate, ferrous gluconate, micronized elemental iron, and as a hydrolyzed protein complex. These can be present as such salt(s) or chelates along with multiple aspartate peptide(s) (either as a free acid and/or as the salt of a different metal (such as potassium, sodium, magnesium or calcium, etc.), or as a copper or iron salt of a multiple aspartate peptide, or both. Multiple aspartate peptide salts of yet other transition metals are also useful.

Transition metals essential for mammalian life with multiple valence states where inclusion of a peptide can be advantageous in controlling product degradation include vanadium, chromium, manganese, iron, cobalt, nickel, copper, and molybdenum. These metals are often added, along with other metals, to vitamin-mineral products. Iron and copper can be especially problematic due, in part, to their high amounts in multivitamin-mineral products. Other transition metals can be found in multivitamin products or foods that are not essential for mammalian life, but which can in any case cause degradation of components of the multivitamin product or the food, and which can benefit from inclusion of a multiple aspartate peptide. In addition, zinc is another essential transition metal that is present in a large amount (U.S. Daily Value 15 mg) in many vitamin-mineral products. Although ionic zinc has only a single valence state (+2), it none the less is known to catalyze, or co-catalyze with other metals, oxidation reactions.

It was found that the salts of several peptides such as multiple aspartate peptides can be hygroscopic to the point of becoming sticky in high humidity environments. It was also discovered that combining such hygroscopic compounds with certain matrices, while not necessarily preventing uptake of water, can none the less produce a novel composition that unexpectedly can be easily handled. One such matrix is microcrystalline cellulose which is commonly used as an excipient in vitamin and mineral products. A method of combining the peptide salt with the excipient was also developed in which the former is dissolved in a suitable solvent, for example water, the excipient added with stirring, and removing the solvent from the mixture, for example by rotary evaporation under reduced pressure or lyophilization. The weight ratio of matrix to the peptide salt can be between about 0.1 to 10, preferably 0.2 to 2. The resulting solid can then be crushed to give the appropriate particle size (for example between 100 and 400 mesh) for homogeneous distribution when added to the other vitamin and mineral ingredients. Other examples of matrices useful for making more easily handled peptide compositions include powdered cellulose, cellulose, kaolin, talc, silica and silicic acid.

Compositions containing the di, tri, tetra or penta-multiple aspartate containing peptide or peptides can also include nutrients and foods that do not necessarily contain explicitly added transition metals (such as iron or copper), but which contain such metals endogenous to food ingredients. In addition, appropriate foods are also those to which a transition metal has been added. The amount of peptide in the composition is that which significantly inhibits degradation (for example, by oxidation, discoloration, or microbial accumulation). Examples of foods which can contain the peptide are, but are not limited to, baby foods and infant formula, ready to eat cereals, formulated bars (such as energy bars), pickled cabbage, carbonated soft drinks, white potatoes (for example canned or frozen), clams (for example canned), crabmeat (for example canned), pickled cucumbers, alcoholic beverages, dressings (such as salad dressing), egg products, fermented malt, beverages (examples: any fruit juice, flavored water containing ascorbic acid), legumes (for example, black-eyed peas, canned lima, pinto, kidney, garbanzo, pink or red beans), mayonnaise, mushrooms (for example canned), oleomargarine, pie filling (for example pecan or strawberry), potato salad, sauces, shrimp, spice extractives in soluble carriers, spreads (for example sandwich spread), fish (for example Gefilte fish). Foods that are high in water are especially appropriate. However, even relatively dry foods can benefit by diminishing the metal catalyzed reactions. Examples of such a multiple aspartate peptides are diaspartic acid, triaspartic acid, and tetraaspartic acid, and their salts as described above. Multiple aspartate peptide or peptides containing amino acid residues other than aspartate, such as those described above, can also be useful.

Compositions containing the di, tri, tetra or penta-peptide or peptides containing two or more aspartates can also be antimicrobial formulations wherein the peptide or peptides are a potentiating and/or sensitizing agent for other antimicrobial compounds. Such formulations can be used for wounds, suture materials, contact lenses, intraocular lenses and the like. These peptide or peptides can be combined with other antimicrobials such as benzalkonium chloride, cetylpyridinum, chloramphenicol, chloroxylenol, chlorohexidine, imipenem, oxytetracydine, penicillin, polymyxin B sulfate, tricolsan among others. Such antimicrobial formulations can be effective against Gram-negative, Gram-positive bacteria, amoeba, fungi and yeasts, and can be used to help prevent and/or decrease biofilm development.

Nutrient product compositions for which multiple aspartate peptides can be effective range from those containing only a single nutrient (for example, a vitamin) and a single transition metal (for example iron or copper) to more complex multi-nutrient and/or multi-metal compositions. An example of a product to which multiple aspartate peptide(s) can be incorporated having two active ingredients is a hematinic containing vitamin C and a form of iron such as those listed above. Hematinic products often contain additional nutrients such as a folate (e.g., folic acid, 5-methyl-tetrahydrofolate, 5-formyltetrahydrofolate) and vitamin B12 among others. These nutrients, like the ascorbic acid in the simpler formulation, can be protected by the inclusion of multiple aspartate peptide(s). Multiple aspartate peptide(s) can be a component of more complex compositions such as multiple vitamin-mineral products containing numerous vitamins and other nutrients (such as amino acids, proteins, nucleic acids, or unsaturated lipids), or micronutrients, (such as carotenoids, e.g. beta-carotene, lycopene, lutein, zeaxanthin, and astaxanthin; polyphenols, e.g. anthocyanidins, catechins, flavonoids, tannins, and procyanidins; and cofactors, e.g., coenzyme Q and glutathione) many of which are susceptible to oxidative degradation, for example by iron or copper. Multiple aspartate peptide(s) can be a component of a multiple vitamin-mineral composition that in addition include natural products or foods as extracts or powders or oils, or any product sold as a supplement. The form of these compositions include, but are not limited to, pills, tablets, capsules, caplets, powders, gels, gummies, chews, effervescents, lozenges, confectionery, etc. While some of these are solid products, others are liquid compositions, examples of which are liquid vitamin products, syrups, mouthwashes, suspensions, complete diets, infant diets, dietary supplements and weight loss products.

Among the vitamins that can components of the multiple vitamin-mineral products of this invention are vitamin C (ascorbic acid and/or its salts), vitamin A (in its various forms such as retinyl acetate, retinol, retinyl palmitate, retinal, vitamin A precursor carotenes, e.g. beta-carotene), vitamin B7 (e.g., biotin), vitamin D (in its various forms such as cholecalciferol, ergocalciferol), 25-hydroxycholecalciferol, 25-hydroxyergocalciferol), vitamin B12 (in its various forms such as cyanocobalamin, methylcobalamin, adenosylcobalamin, hydroxycobalmin), vitamin B5 (in its various forms such as pantothenic acid, calcium pantothenate, and the provitamin pantothenol), vitamin E (in its various forms such as alpha, beta, gamma or delta-tocopherols or mixtures thereof, and/or alpha, beta, gamma or delta-tocotrienols, or mixtures thereof, as well as esters of these such as tocopheryl acetate), vitamin B9 (folate in its various forms such as folic acid, 5-methyl-tetrahydrofolic acid, 5-formyl-tetrahydrofolic acid, 10-formyl-tetrahydrofolic acid, 5,10-methylene-tetrahydrofolic acid, 5,10-methenyl-tetrahydrofolic acid, 5-formimino-tetrahydrofolic acid, tetrahydrofolic acid), vitamin B3 (in its various forms such as niacinamide, nicotinic acid, nicotinamide riboside as well as biomolecules incorporating these such as nicotinamide adenine dinucleotide and its derivatives NADP, NADPH, and NADH), vitamin K (in its various forms such as K1 (e.g., phytomenadione), and K2 (e.g., menaquinones)), vitamin B6 (in its various forms such as pyridoxine, pyridoxine-5'-phosphate, pyridoxal-5'-phosphate, and pyridoxamine), riboflavin (as well as its enzymatically active forms flavin mononucleotide and flavin adenine dinucleotide), and vitamin B1 (thiamine and such forms as its mononitrate and hydrochloride salt, as well as its various phosphate derivatives). Among these, vitamin C, biotin, vitamin A, folate, vitamin B12, vitamin D, vitamin E, and vitamin K, can be especially susceptible to oxidation, particularly if metal catalyzed, for example by iron or copper.

Vitamin-mineral compositions and multivitamin-mineral compositions can in addition to essential and nonessential nutrients also contain excipients that provide a number of useful attributes such as, antiadherents, binders, coatings, colors, disintegrants, flavors, glidants, lubricants, preservatives, sorbents, sweeteners, vehicles. Examples of these include calcium carbonate, magnesium carbonate, dibasic calcium phosphate, tribasic calcium phosphate, calcium sulfate, microcrystalline cellulose, powdered cellulose, dextrates, mannitol, silicic acid, sorbitol, starch, pre-gelatinized starch, or mixtures thereof, agar-agar, alginic acid, croscarmellose sodium, crospovidone, polacrilin potassium, sodium starch glycolate, potato or tapioca starch, other starches, pre-gelatinized starch, clays (such as kaolin and talc), other algins, other celluloses, gums, or mixtures thereof, lactose, sugar, maltitol, gelatin, polyethylene glycol, methyl cellulose, polyvinylpyrrolidone, hydroxypropyl methylcellulose, waxes, shellac, silica, fats (e.g. vegetable stearin), magnesium stearate, stearic acid, and others known to the art.

The present invention also includes a method for stabilizing a food, vitamin, nutrient, or hair from metal catalyzed degradation. The methods involves incorporating an effective amount of multiple aspartate containing di-, tri-, tetra- or penta-peptide or a combination of these into a food, vitamin, or hair-care product. Examples of foods to which the peptides can be added are, but are not limited to, baby foods and infant formula, ready to eat cereals, formulated bars (such as energy bars), pickled cabbage, carbonated soft drinks, white potatoes (for example canned or frozen), clams (for example canned), crabmeat (for example canned), pickled cucumbers, distilled alcoholic beverages, dressings (such as salad dressing), egg products, fermented malt, beverages (examples: any fruit juice, flavored water containing ascorbic acid), legumes (for example, black-eyed peas, canned lima, pinto, kidney, garbanzo, pink or red beans), mayonnaise, mushrooms (for example canned), oleomargarine, pie filling (for example pecan or strawberry), potato salad, sauces, shrimp, spice extractives in soluble carriers, spreads (for example sandwich spread), fish (for example Gefilte fish). Foods that are high in water are especially appropriate. For a product that is in a packing medium, for example canned beans, the volume used for calculating the added the multiple aspartate containing peptide is the combination of the product and the packing medium. The multiple aspartate peptide or peptides can conveniently be added first to the liquid packing medium, or to the combination of the medium with the product. The method of incorporating multiple aspartate peptide(s) can also be used for any combination of individual foods, such as those that are processed or cooked or baked, as well as those that are not heated. The nutrient can be a macronutrient, such as a protein, carbohydrate, or fat (especially unsaturated fats), or a micronutrient, (such as carotenoids, e.g. beta-carotene, lycopene, lutein, zeaxanthin, and astaxanthin; polyphenols, e.g. anthocyanidins, catechins, flavonoids, tannins, and procyanidins; and cofactors, e.g., coenzyme Q and glutathione) or essential such fatty acids, essential amino acids, or vitamins). The effective amount of said peptide is that which is sufficient to slow the rate of degradation of at least one vitamin or nutrient component (for example ascorbic acid) or slows the rate of change in color or of microbial contamination by at least 5%, preferably at least 10%. Examples of methods of this invention are those where the multiple aspartate peptide is of the type described above, e.g. diaspartic acid, triaspartic acid, and tetraaspartic acid. The concentration of Asp-Asp-Asp to be incorporated to achieve this level of decreased rate ranges between about 0.02 mM and about 6 mM. Other multiple aspartate peptide(s) can use more or less than this range depending on their effectiveness relative to Asp-Asp-Asp.

In formulating a composition or optimizing a method the rate of degradation for vitamin formulations can be determined in vitro, for example by dissolution methods set forth in the US Pharmacopeia (USP), or by in vivo pharmacokinetic measurements. In the former case, the rate of loss of the vitamin or nutrient itself, and/or the appearance of degradation products can be measured and compared to an identical experiment lacking the peptide. The USP methodology contains numerous procedures for analysis of content or dissolution rates, etc. that are tailored to the physical form of each product. Among these, for example, Type 1 employs a rotating basket, Type 2 a paddle, Type 3 a reciprocating basket, and Type 4 a flow through cell. In many tests for specific products only a single sample is measured at a specific time. In the context of this invention, samples are analyzed at various times typically over the course of about 120 minutes which encompasses the time of peak absorption of many micronutrients from the digestive tract. Various media such as water, phosphate buffer, simulated gastric fluid, dilute hydrochloric acid, etc. can be used for these test. Some USP tests call for dearation of the medium, but in the context of this invention the medium is best equilibrated to atmospheric oxygen or some other defined mixture of oxygen in another inert gas such as nitrogen. This permits the measurement of the rate of degradation of the components of a product (such as a multiple vitamin-mineral capsule) in a way simulating the influence of consumption by drink a liquid, such as water. Products that are themselves already in the liquid state can also be examined with these methods, except that dissolution itself is not a factor. The liquid product once thoroughly mixed in the medium can still be agitated, or not, depending on the desire to continue the introduction of further atmospheric oxygen. Tests that are not based on USP methods and/or apparatus can also be used. This is useful when examining small volume of homogenous solutions, especially when testing small quantities of peptides in a small vessel.

Many analytical procedures are known in the art for measuring the amount of a specific nutrient or set of nutrients. Among the most useful are those based on gas or liquid chromatography. Some of these procedures are described in various USP monographs, while many others are published in analytical journals. The rate of degradation of a nutrient can be determined by comparing the amount observed in an early sample taken from the measuring apparatus and comparing this to that observed in a later sample. It can also be determined by comparing the amount observed at a given time after mixing with the test medium in comparison to the amount that is measured to be in the product before dissolution. In the latter case, the product is dissolved in such a way that avoids exposure to oxygen and/or incorporates agents that inhibit product oxidation. For example, the initial content of ascorbic acid in a multivitamin-mineral product can be measured by mixing crushed product in thoroughly deaerated 5 mM EDTA under inert gas, and filtering anaerobically.

The rate of degradation can be calculated by comparing the measured content of a nutrient in samples at a various times with either the initial content as measured above, or the highest value within the run, or with the labeled content of the nutrient. The same calculation is performed the presence and absence of the peptide, and the ratio of the two measurements is examined for each of the sampling times. For the purpose of determining the effective amount, comparison of the value for the sample time giving the greatest difference between the ratio in the presence vs absence of peptide is preferred.

In the in vivo method, the appearance of the nutrient in the blood or urine, and/or the appearance of degradation products in blood or urine can be measured. For some nutrients, such as ascorbic acid, in vivo pharmacokinetics are difficult to observe at low dose, and in such cases the use of isotope labeled nutrient and/or measurement of degradation products can be advantageous, as is well known in the art of pharmacokinetics. The degradation can be catalyzed by metals that are added to a food or vitamin, or those that are intrinsic to a food. The rate of degradation of foods or nutrients that are not in the form of tablets or capsules or other such concentrated forms, can be examined by the change in individual components, in color, or by microbial contamination over the intended shelf life by analytical methods well known to the art of food and nutrient technology.

The rate of color change can be measured subjectively by matching colors to a standardize chart, or preferably using a colorimeter, spectrocolorimeter, or spectrophotometer as a function of time. The rate of degradation due to increased rancidity can be examined by several tests including the Peroxide Value (PV) which measure the amount of lipid peroxides; the p-Anisidine (p-AV) and Kreis tests which measures the aldehydes/ketones present in lipids; the Thio-Barbituric Acid Reactivity (TBAR) test which also measures aldehyde content (especially malondialdehye); and the Oxidative Stability Index (OSI) test which is examines stability to air oxidation under accelerated conditions, frequently using the Rancimat method. These methods can be used in the presences and absence of added multiple aspartate peptide(s) to determine the decrease in rate of degradation.

Multiple aspartate peptides and their salts, especially their alkali and alkaline salts, can also be effective for slowing degradation of cosmetic compositions, for example bath preparations, bath soaps and detergents, fragrance preparations, skin cleansing preparations, moisturizing preparations, deodorants, foundations, aftershave lotion, shaving cream, baby shampoos, bubble baths, body and hand, neck and face preparations, creams, lotions, shampoos, makeup products, lipsticks, eye and facial makeup. Hair has been shown to take up copper and iron from a number of sources, including tap water. This leads to increased oxidative degradation of the hair protein, especially in the presence of UV such as in sunlight. Multiple aspartate peptides and their salts, especially their alkali and alkaline salts, can be especially useful in cosmetic preparation used on hair, for example hair shampoos, conditioners, dyes, permanent waves, and colors, etc. They can also be effective in topical or oral drugs such as sunscreens, for products regulated both as a cosmetic and drug such as moisturizing sunscreens, and for other dermatologic drugs. These peptides can stabilize and enhance antioxidants such as ascorbate, tocopherol, and retinol frequently used in and topical or oral drug compositions and cosmetic products.

The degradation of hair and its improvement as a result of using hair products containing multiple aspartate peptide(s) can be assessed by a number of measurements known to the art, for example shine, breakage, and combing force, as well as by analytical techniques such as mass spectroscopy. It is preferred that the decrease the degradation of hair as measured by these or other methods be greater than 5% in comparison to a similar composition lacking multiple aspartate peptide(s).

The multiple aspartate peptides of this invention, whether as salt and/or free acid forms, can be added in powdered solid form to the food, vitamin-mineral supplement, topical or oral drug, or cosmetic. In the case of the vitamin-mineral supplement, this powder can be mixed and made sufficiently homogeneous with the other solid components by the methods well known in the art of pharmaceutical and supplement manufacturing. In the case of foods, topical or oral drug, and cosmetic products having considerable water content, or liquid supplement products such as liquid filled capsules, the added peptide can be dissolved in this water are made homogeneous by mixing. Alternatively, the peptide can be first dissolved in a suitable solvent, for example water or glycerol. The solubility of the peptide, for example a multiple aspartate peptide is increased as a salt form, for example as a sodium or potassium salt.

The effect of transition metals on the degradation (such as by oxidation) of nutrients can, in addition to the inclusion of a multiple aspartate peptide, be further hindered by the use of slowly dissolving form of the metal. The metal can be in the form of a salt with intrinsically low dissolution rate, or a form that is incorporated into a matrix, for example by micro-encapsulation, as is known to the art of bioavailability manipulation. It should be understood that in establishing the effective rate of dissolution of a slowly dissolving form of the metal according to USP methodology it is preferable to measure this in the presence of the other ingredients in a product, rather than simply by itself in water or buffer. It was discovered that dissolution can be influenced by the other product ingredients, in many cases producing faster rates, for example of copper salts, than in water only. The use of a slowly dissolving form of a transition metal, for example copper, can further hinder the destruction of nutrients in addition to the inclusion of a multiple aspirate peptide.

EXAMPLES

Synthesis of Aspartic acid peptides

BOC-Asp-Asp-Bn$_3$: L-Aspartic acid dibenzyl ester 4-toluenesulfonate, 9.7 g (20 mmol) was dissolved with brief heating in 12.5 ml anhydrous DMF. To this, now at ambient temperature, was added a solution of 8.4 g (20 mmol) Boc-L-aspartic acid ß-benzyl ester N-hydroxysuccinimide ester in 12 ml anhydrous DMF, followed by 2.8 ml (~21 mmol) triethylamine with stirring. A 10-fold dilution of a sample into water measured pH 4.5 with indicator paper. The reaction was followed by injection of a 10-fold dilution into MeOH onto a Prodigy C-18 150×4.6 mm HPLC column eluted at ambient temperature with ACN/0.1% TFA (11:9) at 2 ml/min with photodiode array detection. Analysis at 83 minutes indicated that all of both starting materials had been consumed. Solvent was removed by rotary evaporation at reduced pressure, 60 ml of ethyl acetate added, the resulting solution washed with 3×75 ml of water. Solvent was removed by rotary evaporation at reduced pressure and the product dried under high vacuum over $P_2O_5$ to give 11.6 g of BOC-Asp-Asp-Bn$_3$ as a light tan powder.

Asp-Asp-Bn$_3$: All of the above BOC-Asp-Asp-Bn$_3$ was dissolved in 20 ml of anhydrous dimethoxyethane under a blanket of inert gas and placed on ice. To this was quickly added 25 ml of HCl in anhydrous dimethoxyethane (saturated by 45 minutes of bubbling HCl on ice) with vigorous stirring. After 45 minutes the reaction was removed from the ice and allowed to warm to room temperature. HPLC as above indicated complete disappearance of starting material by 115 min. Solvent was removed by rotary evaporation at reduced pressure with two further additions of 25 ml each of fresh DME to facilitate removal of HCl, and the solid kept under high vacuum over NaOH pellets to give a thick orange oil that solidifies on storage.

BOC-Asp-Asp-Asp-Bn$_4$: All of the above Asp-Asp-Bn$_3$ was dissolved in 10 ml anhydrous DMF to which was added 8.0 g Boc-L-aspartic acid ß-benzyl ester N-hydroxysuccinimide ester in 11 ml anhydrous DMF. The reaction was initiated by titration with Et$_3$N to pH 4.5 to 5.0 (sample 10-fold diluted in water measured with indicator paper), and stirred at room temperature. The pH is maintained within this region using additional Et$_3$N. After 2 hours consumption of reactants is near completion as indicated by HPLC of a 50-fold dilution in MeOH using the above system, but with ACN/0.1% TFA (1:2), while product is eluted more rapidly with a 53:47 solvent ratio. Solvent was removed by rotary evaporation at reduced pressure to give a thick slurry which was dissolved in 60 ml of ethyl acetate, and extracted four times with 70 ml each of water. Solvent was evaporated under reduced pressure, 30 ml of n-BuOH added and removed by further rotary evaporation, and the product put under vacuum over $P_2O_5$. This material can be purified by crystallization from warm methanol or ethanol and cooling to −20° C.

Deprotection of BOC-Asp-Asp-Asp-Bn$_4$ can be performed in either order, but hydrogenolysis of the benzyl groups first has the advantage of requiring less catalyst due to the presence of the protected amino group.

Asp-Asp-Asp-Bn$_4$ HCl: All of the above BOC-Asp-Asp-Asp-Bn$_4$ was dissolved in 24 ml anhydrous DME and cooled in an ice bath, and 26 ml of HCl saturated in anhydrous dimethoxyethane (at 0° C.) added with stirring. At 50 min the mixture was allowed to warm to room temperature, and after 90 min solvent was removed by rotary evaporation at reduced pressure. To remove residual HCl, 30 ml of DME was added and removed by rotary evaporation, again this was repeated, and product placed under vacuum over NaOH pellets.

Asp-Asp-Asp: All of the above Asp-Asp-Asp-Bn$_4$ HCl was dissolved in 220 ml EtOH plus 6 ml DME, 6 g 10% Pd on charcoal was added, and the reaction bubbled at atmospheric pressure and ambient temperature with vigorous stirring. The disappearance of starting material, less benzylated intermediates and appearance of toluene was monitored by the above HPLC system using ACN/0.1% TFA (53:47). By 90 min all of the peaks absorbing at 255 nm (aside from toluene) were no longer detected, and the reaction mixture was centrifuged for 15 min at 500×g. The supernatant was decanted, catalyst washed twice with 25 ml EtOH and the combined material filtered through a 0.45 micron TFE filter. Solvent was removed from the filtrate by rotary evaporation at reduced pressure, and placed under vacuum over $P_2O_5$ to give 8.2 g of a golden semisolid.

BOC-Asp-Asp-Asp: Crystallized BOC-Asp-Asp-Asp-Bn$_3$ (2.7 g) was fully dissolved in 30 ml anhydrous ethanol, 0.27 g of 10% Pd on charcoal was added, and hydrogen bubbled with stirring at ambient temperature and pressure. By 35 min all the starting material and intermediate levels of benzylation were consumed a judged by the above HPLC system using ACN/0.1% TFA (53:47), the reaction filtered through a 0.22 micron TFE filter, and washed with an additional 10 ml EtOH. Rotary evaporation at reduced pressure, and exposure to high vacuum over P$_2$O$_5$ gave 1.8 g of BOC-Asp-Asp-Asp as a colorless hygroscopic glass.

Asp-Asp-Asp: All of the above BOC-Asp-Asp-Asp was dissolved in 50 ml anhydrous DME and placed in an ice bath. To this was added with stirring 50 ml of DME freshly saturated on ice with HCl gas. After 30 min all of the BOC protecting group had been removed as measured by the above HPLC system using ACN/0.1% TFA (1:8), and the mixture rotary evaporated at reduced pressure to a about 10 ml, whereupon the product precipitated. Unexpectedly, further product can be driven out of solution by brief warming (for example, to about 50° C.), and obtained by rapid filtration while still warm. After exposure to high vacuum over both P$_2$O$_5$ and NaOH pellets, the HCl salt of Asp-Asp-Asp is obtained as a hygroscopic powder. This material is typically greater than 90% pure based on 230 nm absorbance area in the above HPLC system using 100% of 0.1 mM TFA as mobile phase. It can be further purified by preparative HPLC on Kromasil C18 using 0.1 mM TFA to give the TFA salt after evaporation. Triaspartic acid can be crystallized from water after adjustment to about pH 3.

1,1,1-His-Asp-Asp and 1,1,1-Ala-Asp-Asp: These compounds were synthesized by methods similar to the above, but using N$^\alpha$,N$^{im}$-Bis-Boc-L-histidine N-hydroxysuccinimide ester and Boc-L-alanine N-hydroxysuccinimide ester, respectively, for addition of the third residue to Asp-Asp-Bn$_3$. In the case of Ala-Asp-Asp, catalytic hydrogenolysis of the benzyl protecting groups was performed before the final removal of BOC group.

COMPARATIVE EXAMPLES

The following studies illustrate the problem of decomposition of the constituents of several vitamin-mineral products. The dissolution studies described herein used a U.S. Pharmacopeia (USP) type 2 apparatus with 500 ml distilled H$_2$O at 37° C. stirred at 50 RPM. Although some USP methods for several vitamins calls for a measurement only at 45 min, 10, 80 and 115 minutes samples were also taken and filtered through a 0.22 micron PES membrane and injected into a reversed phase HPLC system that was monitored with photodiode array and fluorescence detectors in series. Oxygen concentration was monitored with a Clarke electrode calibrated against argon and air sparged water at 37 C. The disappearance of several components was gauged against a mixture of pure standards of known concentration.

Figure 2:
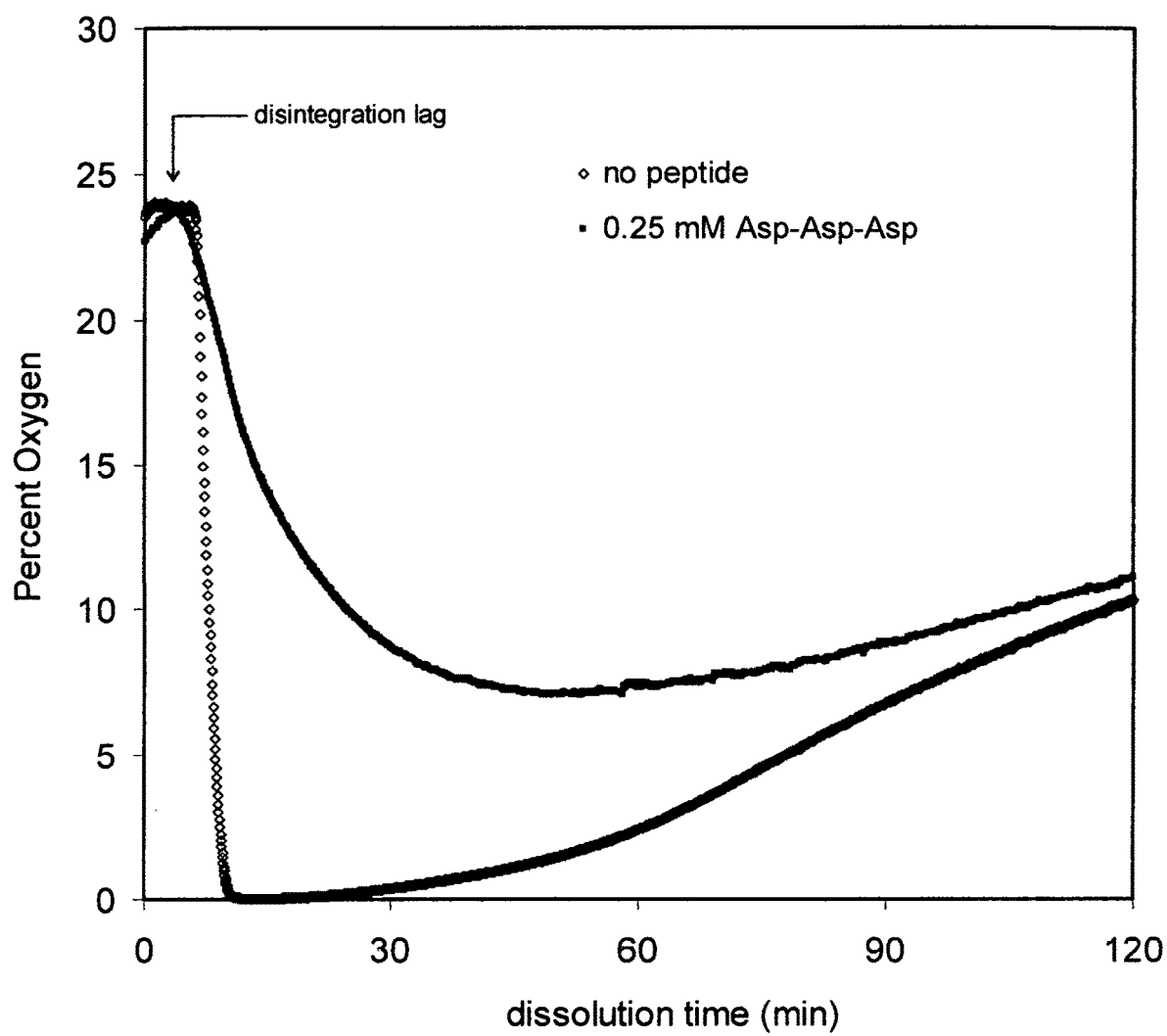
FIG. 2 shows the oxygen consumption during dissolution of multivitamin-mineral supplement 1a over time in the absence and presence of 0.25 mM or Asp-Asp-Asp.

Product #1a: In the case of multivitamin-mineral products the inventors found that during a dissolution study all but about 5% of the labeled amount of ascorbic acid in a commercially available tablet designated for use by women formulated with 2 mg of copper (as CuSO$_4$) and 18 mg of iron (as ferrous fumarate) was decomposed within 45 minutes. Well before the time of the first sample at 10 minutes these tablets had already largely disintegrated. The total initial content of vitamin C in this and other products was determined by dissolution of a crushed tablet in thoroughly argon sparged 5 mM EDTA mixed with further vigorous bubbling of argon and injection of a sample filtered under argon into the HPLC system. Product 1a was found to contain on average 120% of the labeled amount of 60 mg per dose (i.e., 72 mg), all of which was irreversibly destroyed by 80 minutes in the standard dissolution test (FIG. 1). Importantly, dehydroscorbate was not detected at any time. This loss of ascorbic acid was accompanied by a rapid decrease in the oxygen concentration of the aqueous dissolution medium which reached nearly 0 percent by about 10 minutes. With continued stirring by the USP paddle, O$_2$ was slowly reintroduced after 45 minutes but did not reestablish air saturation even by 115 minutes (FIG. 2). A nearly identical product (#1b) produced by the same manufacturer, but formulated with cupric oxide instead of the cupric sulfate lost ascorbic acid more slowly at between about 0.4% to 0.9% per minute between the 10 and 45 minute samples. The oxygen consumption due to dissolution of this tablet containing CuO was also slower in reaching a minimum of about 10% after about 70 minutes. The profile of ascorbate and oxygen decreases due to product #1b were very similar to those of Product #1a if 2 mg of copper as CuSO$_4$ was added to the 500 ml of water prior to the tablet. The rate produced by Product #1b in the presence of 1 mg of copper (as CuSO$_4$) added to the dissolution medium was slower than with 2 mg, as was the maximum rate of oxygen consumption.

Figure 3:
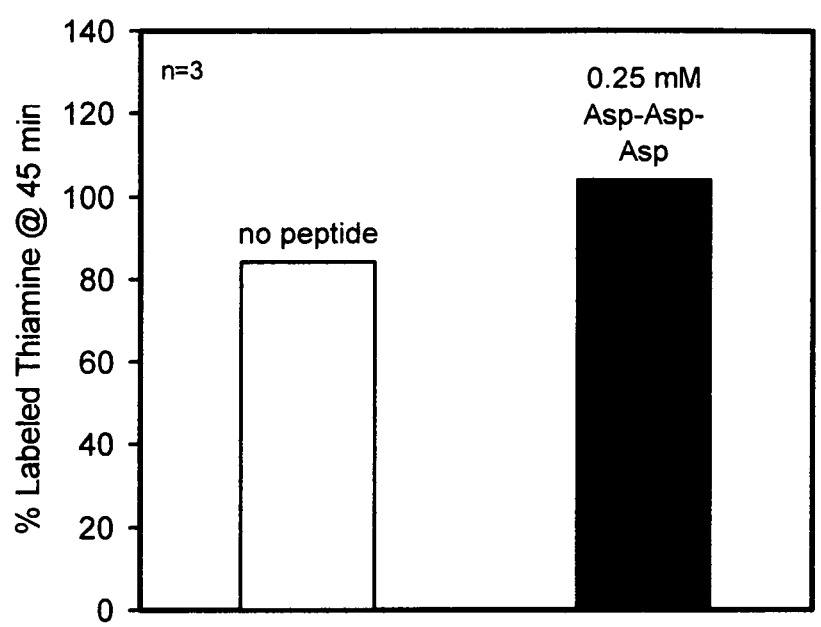
FIG. 3 shows the amount of thiamine recovered at 45 minutes (expressed as a percentage of the labeled content) from a USP type 2 dissolution experiment containing a commercially available multivitamin-mineral supplement (1a) in the absence and presence of 0.25 mM Asp-Asp or Asp-Asp-Asp over time.

The total content of the thiamin (vitamin B1) in the above product #1a was determined using crushed tablets and was found to average about 125% higher than the 2.4 mg labeled amount. Examining the filterable thiamin during USP type 2 experiments as above showed that the amount in solution at 10 minutes was only 67% of the total actual content on average (84% of the labeled content). This did not change significantly after 45 minutes of dissolution (FIG. 3).

The appearance of folic acid in Product #1a during USP type 2 dissolution experiments was influenced by two factors. First, the great majority of the total folic acid content remained sequestered in non-filterable particulate matter. The actual final content of folic acid was determined after 150 minutes by adding sodium hydroxide to a final concentration of 25 mM, disodium EDTA to a final concentration of 5 mM, and sonicating the mixture for 5 minutes prior to 0.22 micron filtration. This indicated that the total amount of intact folic acid at 150 min was typically about 160% of the 0.40 mg labeled value. However, a second factor was observed in that the p-aminobenzoyl-glutamate side chain of some folic acid is also oxidatively cleaved as detected by its fluorescence on elution from the HPLC column. This was found to be about 9% of the labeled amount of folic acid. Sampling the dissolution experiment as a function of time shows that after 10 minutes only less than about 5% of the labeled amount folic acid appears in the filtrate. By 45 minutes this increased slightly to about 10% of the labeled value. Thereafter, the amount in the filtrate rapidly increases, but still only up to about 40% by 115 min. The time at which folic acid starts to appear more rapidly in solution approximately corresponds to when the dissolved oxygen begins to increase again as a result of stirring by the USP paddle. If at any time during a dissolution experiment the solids are harvested by centrifugation and treated by sonication with 25 mM NaOH/5 mM Na$_2$EDTA, folic acid can be found in the filtrate in an amount similar to that detected at the end of a typical run at 115 min. This shows that in Product #1a folic acid is sequestered in the solids and only very slowly leaches into solution. The course of folic acid release into solution is very different with Product #1b (which incorporates insoluble cupric oxide instead of soluble cupric sulfate).

With these tablets the final total content of folic acid is also about 160% of the labeled value as with #1a. However, even after 10 minutes of dissolution around 55% of the labeled value typically appears in a filtered sample, which increases to about 65% after 45 minutes of dissolution and on average does not further increase even in a 115 minute sample.

Product #2: A multivitamin-mineral supplement tablet from a second manufacturer also designated for use by women was labeled to contain 2 mg of copper (as $CuSO_4$) and 18 mg of iron as ferrous fumarate was also examined. The total vitamin C content as determined above was on average 225 mg, i.e. 125% of the labeled amount (180 mg, 300% of the Daily Value). During USP type 2 dissolution testing as above little ascorbate was present in the 10 minute sample, but increased to a maximum in the 45 minute sample and then slowly declined. A. This maximum amount was on average about 79% of the labeled amount, or 63% of the actual initial content. This represents a loss of about 83 mg of ascorbic acid on average. The concentration of dissolved oxygen falls to nearly zero after only a few minutes, and (in contrast to Product #1) remained very low despite continued stirring with the USP paddle.

Product #3: A tablet from yet another manufacturer labeled to contain 150 mg (250% of the Daily Value) of vitamin C and 2 mg of copper (as amino acid complex), but no explicit iron, did not disintegrate as quickly as those from manufacturers 1 or 2. Probably as a result, many of the nutrients did not quickly appear in solution. In particular, ascorbic acid did not reach a maximum concentration until between 45 and 80 minutes, where it was only 38% of the labeled amount. The total content of ascorbic acid in Product #3 was not determined, thus the missing 62% represents the destruction of a minimum of 93 mg of vitamin C.

Product #4: A tablet from a fourth manufacturer which contained neither any copper nor significant iron did not release much of its nutrient content by 10 minutes of dissolution: for example of the labeled amount of ascorbic acid (110 mg) only 7% was found in a sample at this time. However, the 45 minute sample showed 151% of the labeled amount which was nearly the same as measured at 80 minutes (157%). Over the course of the dissolution run dissolved oxygen slowly decreased only to about 68% of its initial value. This product which contains no transition metals did not appear to suffer from meaningful destruction of its vitamin C or its other nutrients.

The above results show the vitamin C in a multivitamin-mineral supplement can be rapidly degraded especially in the presence of copper and/or iron. The amount of the loss may be limited by the amount of dissolved oxygen present in the dissolution vessel, or in the liquid used to consume the supplement product. With water equilibrated to air at 37 C this amounts to around 90 mg (0.51 mmole). The ascorbic acid in products actually containing less than this can be completely and irreversibly destroyed, for example 100% of the U.S. Daily Value is 60 mg. For products containing substantially greater than 90 mg of vitamin C, some can remain after the oxygen is consumed, although leaving behind considerable ascorbate degradation products. In addition, as described above, other components in the vitamin-mineral product are also decomposed.

Example 1 Inclusion of small peptides containing two of more aspartic acid residues was unexpectedly found to greatly increase the amount of ascorbic acid in samples taken from typical USP type 2 dissolution experiments with multivitamin/mineral supplements. With Product #1a but where 0.125 mmole tetra-sodium 1,1,1-triaspartate was initially present in the 500 mL (Asp-Asp-Asp concentration=0.25 mM, initial pH ~6.5), the ascorbic acid recovered after 45 min was remarkably about 16-fold higher than with water only (FIG. 1). The rate of oxygen consumption is dramatically decreased, with about a third of the original concentration remaining even after 45 min (FIG. 2). This greatly increased stability allows more time for the intestinal absorption of this and other vitamins. In this particular experiment the molar ratio of copper (2 mg, 0.0315 mmol) to triaspartic acid peptide is about 1:4, and the molar ratio of copper to all aspartic acid residues is about 1:12. The amount of thiamine present at 45 minutes increased to an average of 83% of the actual content of these tablets (104% of labeled content) in comparison to 67% (84% of labeled content) without Asp-Asp-Asp (FIG. 3). Increasing amount of peptide can further benefit the maintenance of ascorbic acid and thiamine. Folic acid release during dissolution was considerably enhanced by inclusion of 0.25 mM Asp-Asp-Asp in the medium. Product #1a showed about 55% of the labeled folic acid amount in the 10 minute sample and about 70% in the 45 minute sample filtrates. This is similar to the results with the cupric oxide containing Product #1b in the absence of any peptide. The amount of p-aminobenzoyl-glutamate measured in the final sonicated sample decreased to half of that in the absence of the peptide. Product #1a also contained caffeine. Without added Asp-Asp-Asp peptide a portion of this was oxidized over time to 1,3,7-trimethyluric acid (8-oxo-caffeine) as determined by comparison to authentic standard. In the presence of 0.25 mM Asp-Asp-Asp the extent of this oxidation was more than halved.

Example 2 USP type 2 dissolution experiments were performed on Product #1b formulated with CuO, but with either 1 or 2 mg of copper added to the water medium as $CuSO_4$ and also tetra-sodium 1,1,1-triaspartate in concentrations varied from 0.05 to 0.5 mM. The rate of loss of ascorbic acid in the presence of 2 mg of added copper and 0.25 mM Asp-Asp-Asp was similar to that found with Product #1a (which contains 2 mg of Cu as $CuSO_4$ endogenously) in the presence of 0.25 mM Asp-Asp-Asp. This shows that the effect of the Asp-Asp-Asp peptide is the same whether the soluble copper is in the dissolution medium or from the tablet itself. The concentration of Asp-Asp-Asp required for 50% of maximal effectiveness in preventing ascorbate loss was calculated by fitting to a hyperbolic response curve to be about 0.05 mM. Thus, the maximal benefit of Asp-Asp-Asp in this experiment requires a higher mole amount than the mole amount of the copper. The results with 1 mg of copper added to the water medium as $CuSO_4$ were consistent with this finding in that a somewhat lower concentration of Asp-Asp-Asp was required for half maximal effect in preventing loss of ascorbate.

Example 3 A USP type 2 dissolution experiment was performed on Product #1b formulated with CuO, but with a $Cu_{(1/3)}Ca_2$-1,1,1-triaspartate/crystalline cellulose powder added to the water medium simultaneously with the tablet. The weight ratio of the $Cu_{(1/3)}Ca_2$-triaspartate to cellulose was 1:1, and the final concentration of copper in the medium was equivalent to 1 mg and the concentration of Asp-Asp-Asp was 0.093 mM. The profile of ascorbate loss, and appearance of thiamine and folic acid was not significantly different from similar runs as described in Example 2 with 1 mg of copper and 0.1 mM Asp-Asp-Asp not added as a preformed calcium-copper salt. Thus, the effectiveness of Asp-Asp-Asp is not influenced by its being provided as in a cellulose matrix.

Example 4 Inclusion of tetra-sodium 1,1,1-triaspartate (1 mM) in the dissolution of product #2 increased the average recovery of thiamine at 45 minutes by 20% over that obtained with no added peptide. The ascorbate appeared in solution more quickly in the presence of Asp-Asp-Asp, and the average recovery of ascorbic acid from product #2 (which is labeled to contain 300% DV) at 45 minutes in these experiments was increased by 16% in comparison to those performed without a peptide.

Example 5 A USP type 2 dissolution of Product #1a was performed with 0.125 mmole tri-sodium 1,1-diaspartate initially present in the 500 mL ($Asp_2$ concentration=0.25 mM, pH ~6.5). The ascorbic acid recovered after 45 min was greater than with no $Asp_2$ but somewhat less than in the presence of 0.25 mM Asp-Asp-Asp (FIG. 1). The profile of folic acid appearance in solution was greater than without any peptide, and similar to that liberated by 0.05 mM Asp-Asp-Asp. The profile of p-aminobenzoyl-glutamate formation was suppressed in comparison to without any peptide, and similar to 0.05 mM Asp-Asp-Asp. The profile of thiamine appearance in solution was not significantly different than without peptide. The rate of oxygen consumption was less than without a peptide. Thus, while $Asp_2$ is effective in making some vitamins more available in solution and protecting them from degradation, it is less effective per weight of peptide than Asp-Asp-Asp, even though the latter has a 46% higher molecular weight. Simple aspartic acid (i.e., not formed into a peptide) provided no improvement in maintenance of ascorbic acid, or decreased the rate of oxygen consumption.

Example 6 A USP type 2 dissolution of Product #1a was performed with 0.125 mmole tri-sodium 1,1,1-His-Asp-Asp initially present in the 500 mL (His-Asp-Asp concentration=0.25 mM, pH ~6.5). No improvement in maintenance of ascorbate or thiamine, diminishing oxygen consumption, or oxidation of other components was observed.

Examples 7-11 The effectiveness of multiple aspartate peptides on preventing the decomposition of various vitamins was examined in homogeneous solutions. Aqueous solutions of air saturated buffer, peptide, one or more vitamins, and metal salt (e.g. ferrous chloride or cupric sulfate) were combined and incubated at 37 C, unless otherwise stated. Samples were injected into the HPLC system as a function of time and monitored by a photodiode array detector.

Figure 4:
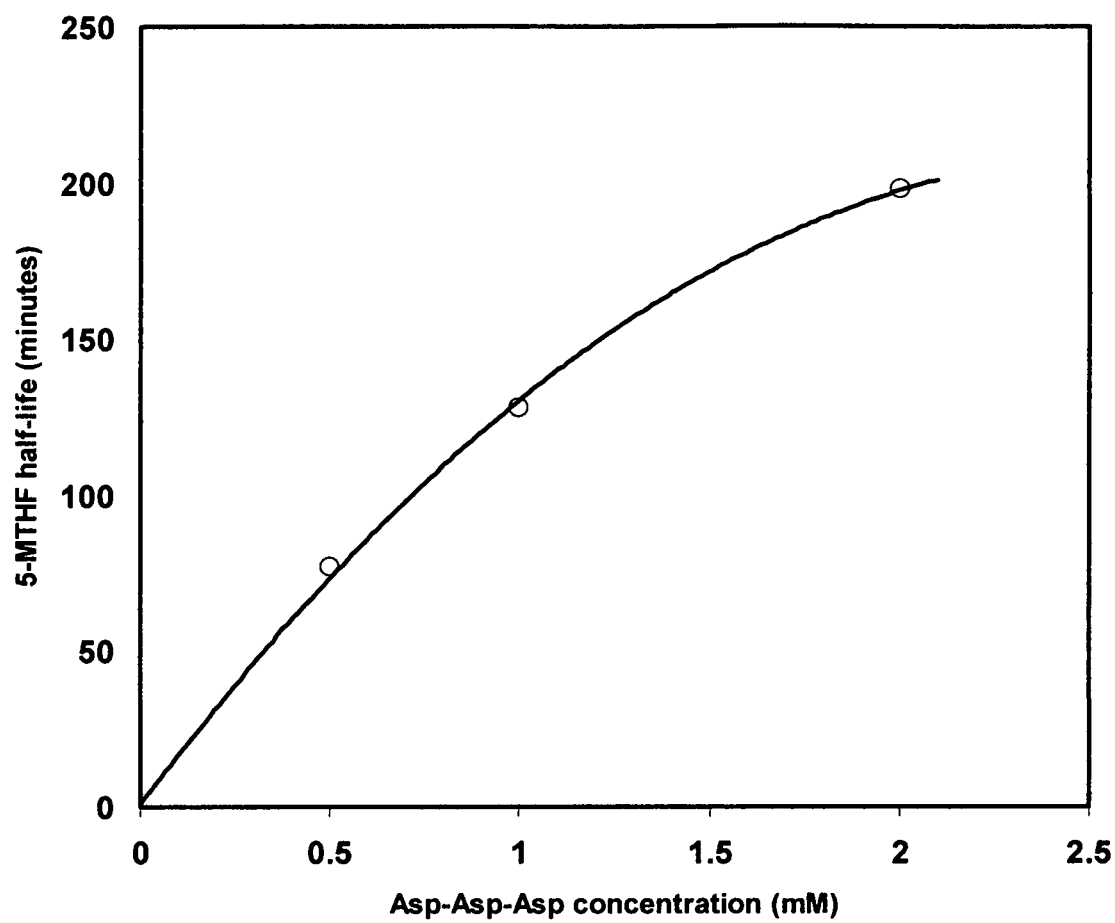
FIG. 4 shows the half-life of 5-methyltetrahydrofolate as a function of Asp-Asp-Asp concentration in a homogenous air equilibrated solution of 0.15 mM $CuSO_4$ in 10 mM HEPES pH 7.2 at 37 C.

Example 7 The decay of 25 µM calcium 5-methyltetrahydrofolate (5-MTHF) in 10 mM HEPES pH 7.2 buffer in the presence of peptide and 150 µM cupric sulfate (added last) was measured. In control runs without any peptide, cupric sulfate in concentrations of above 40 µM resulted in complete loss of 5-MTHF within the first two minutes of incubation. Including either tetra-sodium 1,1,1-triaspartate or penta-sodium 1,1,1,1-tetraaspartate increased the half-life of the 5-MTHF in a concentration dependent manner (FIG. 4); with 2 mM giving 198 and 178 minutes respectively. Thus, while in this situation Asp-Asp-Asp and $Asp_4$ are similarly effective at a given molarity, the former due to its lower molecular weight has the advantage in terms of weight of peptide per volume. Tri-sodium 1,1-diaspartate at 2 mM gave a concentration dependent 5-MTHF half-life of 72 minutes at 2 mM. At a concentration of 0.5 mM Asp-Asp-Asp gave a half-life longer than $Asp_2$. The stability of 5-MTHF improves somewhat with even higher concentrations of peptide; for example with 3 mM and 4 mM $Asp_2$ its half-life increases to 87 and 100 minutes, respectively. Thus, diaspartic acid is not quite as effective under these conditions as Asp-Asp-Asp, even on a per weight basis. The dipeptides 1,1-aspartyl-glutamic acid, 1-aspartyl-glycine, and 1,1-glutamyl-aspartic acid gave a half-lives that were between 50 to 75 percent of that of $Asp_2$ (each determined at 0.5 mM as neutral sodium salts, and 25° C.).

The decomposition of 5-MTHF is slower in acidic solutions than at neutral pH, and this was found even in the presence of cupric ions. For example, at 37 C in 1 mM HCl (as can be found in the stomach) and in the presence of 150 µM cupric sulfate the time to half decomposition of 5-MTHF was observed to be around 20 minutes (this decay curve was not well described by a 1st-order decay). With 3 mM 1,1,1-triaspartic free acid also present the time to half decomposition was increased to around 30 minutes. Thus, while this form of folate is more stable in acid, the effectiveness of this multiple aspartate peptide is less than near neutral pH.

Figure 5:
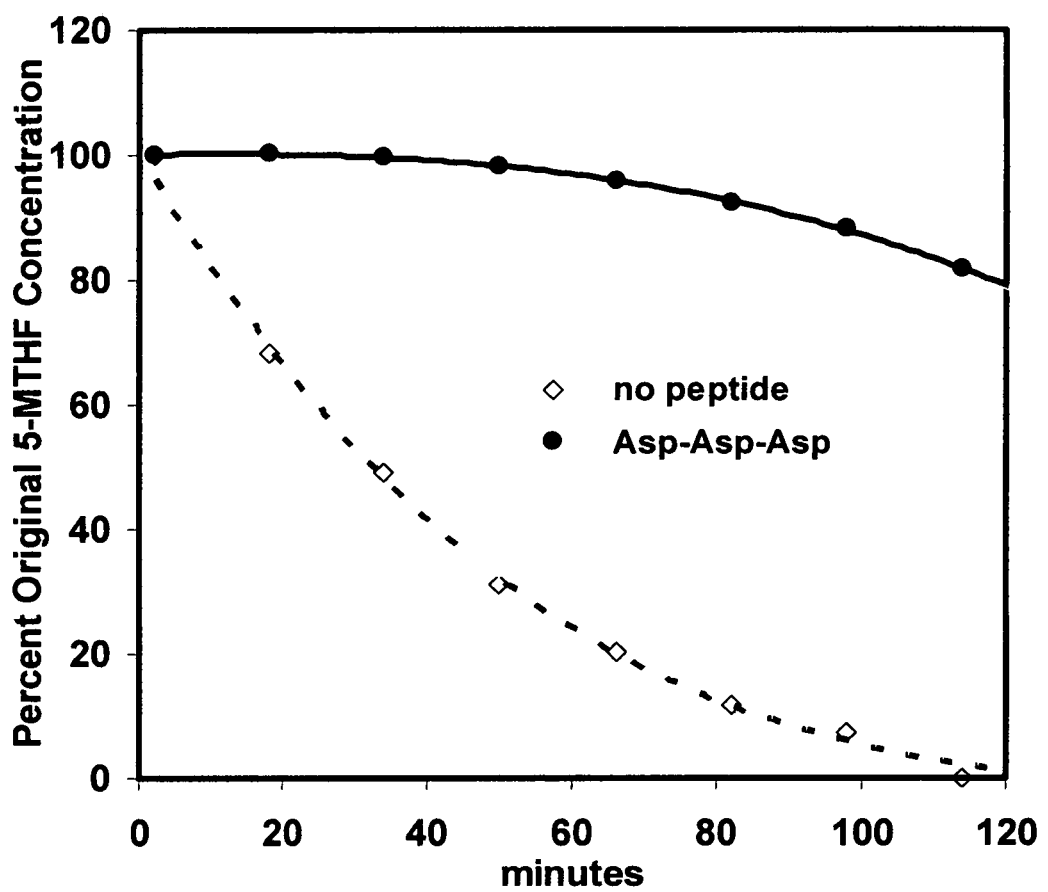
FIG. 5 shows the loss of 5-methyltetrahydrofolate in a homogenous air equilibrated solution of 3 mM ferrous iron in MES buffer pH 6.2 at 37 C in the absence and presence of 3 mM Asp-Asp-Asp tetrasodium salt.

Example 8 The decay of 25 µM calcium 5-methyltetrahydrofolate (5-MTHF) in 40 mM MES pH 6.2 buffer in 3 mM ferrous chloride (freshly prepared and added last) was measured. In the absence of a peptide a half-life of 5-MTHF decay of 25 minutes was found. In the presence of presence of 3 mM tetra-sodium 1,1,1-triaspartate no significant loss of 5-MTHF was observed for about 50 minutes, and then deceased by about 17% per hour (FIG. 5).

Example 9 The effect of cupric sulfate (150 µM) on the combination of folic acid (10 µM) and sodium ascorbate (5 mM) was examined in the following various buffers. Reactions were continuously but slow sparged with air so that oxygen would not become limiting.

In 10 mM MES pH 6.2 about 35% of the initial ascorbic acid was decomposed by 10 minutes and 90% decomposed by 26 minutes. In the presence of 3 mM tetra-sodium 1,1,1-triaspartate 35% of the ascorbate remained even by 32 minutes. In these same reactions folic acid was more than 98% decomposed by 26 minutes in the absence of multiple aspartate peptide, but 75% remained even after 82 minutes in the presence of 3 mM Asp-Asp-Asp. In 50 mM MES pH 5.5 the ascorbate was completely consumed by 26 minutes in the absence of any peptide, but this required 47 minutes in the presence of 3 mM Asp-Asp-Asp. In these same reactions folic acid was more than 85% consumed by 26 minutes, but remained constant thereafter in the absence of aspartate peptide. This indicates that the presence of ascorbate and not just oxygen and copper is involved in the decomposition of the folic acid. In the presence of 3 mM Asp-Asp-Asp at more than 50% of the folic acid was recovered even after 82 minutes of incubation.

Similar reactions were also performed in 10 mM HEPES pH 7.2 in which the ascorbate was observed to be completely lost by 21 minutes in the absence of an aspartate peptide. In the presence of 1 and 3 mM 1,1,1-triaspartate (as the tetra-sodium salt) only 33% and 18% of the initial ascorbate, respectively, was lost after 2 hours.

Figure 6:
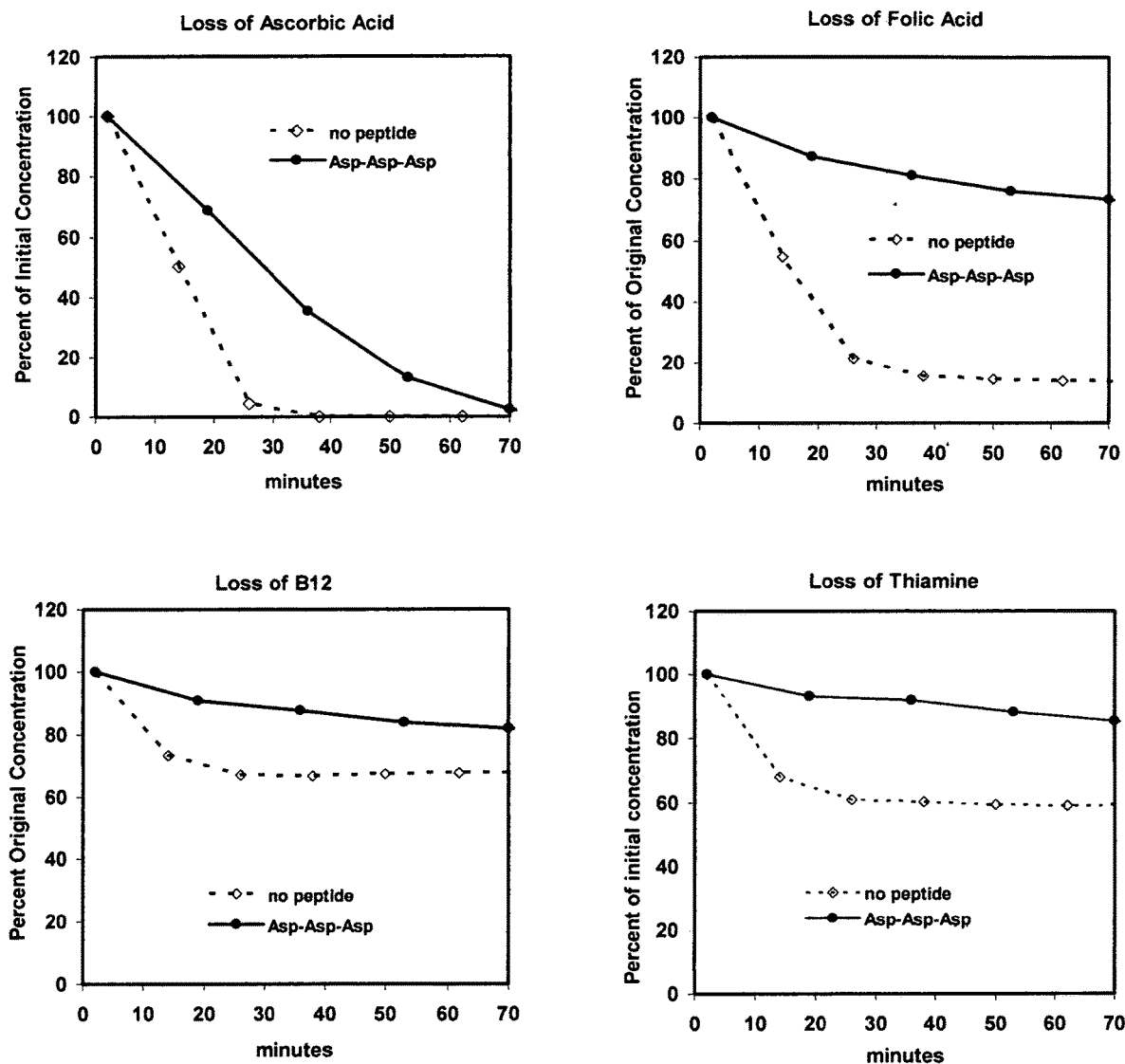
FIG. 6 shows the loss of ascorbic acid, folic acid, thiamine and vitamin B12 all together in a homogenous air equilibrated solution of 150 micromolar cupric sulfate in MES buffer pH 6.2 at 37 C in the absence and presence of 3 mM Asp-Asp-Asp tetrasodium salt.

Example 10 The effect of cupric sulfate (150 µM) on the combination of vitamin B12 (10 µM cyanocobalamin), thiamine (1.5 mg/ml as HCl salt), folic acid (10 µM) and sodium ascorbate (5 mM) was examined in 10 mM MES pH 6.2 slowly sparged with air (FIG. 6). Vitamin B12 rapidly decreased within the first 26 minutes by about 43% in the absence of an aspartate peptide, but remained constants thereafter presumably due to concomitant depletion of ascorbate. In the presence of 3 mM 1,1,1-triaspartate (as the tetra-sodium salt) the loss of Vitamin B12 was limited to about 20% even after 2 hours. Thiamine also rapidly disappeared by 40% over the first 26 minutes and then remained constant in the absence of an aspartate peptide. However, with 3 mM Asp-Asp-Asp included only 8% was lost at 36 min. It should be clear, however, that these particular losses of vitamins do not represent all circumstances which may have more or less ascorbic acid present and different concentrations of copper and oxygen availability.

Example 11 The effect of 1,1,1-Ala-Asp-Asp on the decay of sodium ascorbate in 10 mM HEPES pH 7.2 at 37 was compared with 1,1,1-triaspartate in the presence of 63 µM cupric sulfate (equivalent to 2 mg of elemental copper per 500 mL). At a peptide concentration of 0.25 mM Ala-Asp-Asp the 1st-order rate of ascorbate loss was almost twice as fast as Asp-Asp-Asp. This difference is somewhat offset by the ~12% lower molecular weight of the former.

Example A Tetra-sodium-1,1,1-triaspartate: 1,1,1-Triaspartic free acid (117 mg of 1.5 hydrate, 0.30 mmoles) was dissolved in 5.0 ml of water at ambient temperature, 4 ml of 3 M sodium hydroxide (1.2 mmoles) was added, and the mixture stirred until completely in solution of pH 6 to 7. This was rotary evaporated under reduced pressure at 38° C. to a solid that was placed under high vacuum over $P_2O_5$ for 24 hours to give 135 mg colorless clear flakes. When left open to the atmosphere, these quickly gained 14% in weight of water and became sticky.

Example B Tetra-sodium-1,1,1-triaspartate on microcrystalline cellulose: All of the tetra-sodium-1,1,1-triaspartate from Example A was dissolved in 5 mL of water, 135 mg of microcrystalline cellulose added, and mixed. This was rotary evaporated under reduced pressure at 38° C. to a white solid that was placed under high vacuum over $P_2O_5$ for 24 hours. The resulting material was crushed to pass through a 200 mesh sieve. On exposure to the atmosphere this gained 11% in weight as water, but none the less remained free flowing.

Example C Tetra-potassium-1,1,1-triaspartate: 1,1,1-Triaspartic free acid (117 mg of 1.5 hydrate, 0.30 mmoles) was dissolved in 5.0 ml of water at ambient temperature, 4 ml of 3 M potassium hydroxide (1.2 mmoles) was added, and the mixture stirred until completely in solution of pH 6 to 7.

Example D $Calcium_{1.5}$-1,1,1-triaspartate: 1,1,1-Triaspartic free acid (117 mg of 1.5 hydrate, 0.30 mmoles) was dissolved in 5.0 ml of water at ambient temperature, 33 mg (~0.45 mmoles) of calcium hydroxide was added, and the mixture sonicated until completely in solution of pH 6 to 7. This was rotary evaporated under reduced pressure at 38° C. to give a clear solid that was placed under high vacuum over $P_2O_5$ for 24 hours resulting in free flowing flakes. On leaving open to the atmosphere at ambient temperature this regained ~10% weight over the next several days due to uptake of water. Over the next several months the weight was found to fluctuate by a few percent with changes in ambient humidity, but remained free flowing flakes that were never sticky. On exposure to 90% RH for 24 hours this material clumped slightly, but was easy to break up and was not sticky. Nutrient preparations containing, for example, 0.05 mmoles, 0.10 mmoles, 0.125 mmoles, 0.25 mmoles, or 0.50 mmoles of 1,1,1-triaspartate by addition of this material would also add about 3.0 mg. 6 mg, 7.5 mg, 15 mg, and 30 mg to the calcium content from other ingredients, respectively.

Example E $Magnesium_{1.5}$-1,1,1-triaspartate: This was produced in the same manner as the above calcium salt, but using magnesium hydroxide instead of calcium hydroxide. Nutrient preparations containing, for example, 0.05 mmoles, 0.10 mmoles, 0.125 mmoles, 0.25 mmoles or 0.50 mmoles of 1,1,1-triaspartate by addition of this material would also add about 1.8 mg. 3.6 mg, 4.5 mg, 9.1 mg, and 18.2 mg to the magnesium content from other ingredients, respectively.

Example F $Cupric_{1/4}$-$Mg_{1/4}$-1,1,1-triaspartate: Cupric sulfate·$5H_2O$ (34 mg, 0.136 mmoles) was dissolved in 0.4 ml water and 1M sodium carbonate added with rapid stirring to give between about pH 8.5 to 9.5, the mixture centrifuged, and the supernate decanted and discarded. The precipitate was resuspended in 0.5 ml ice-cold water, recentrifuged, and the second supernate discarded. To this was added 0.54 mmoles of 1,1,1-triaspartic free acid as a 60 mM aqueous solution and vortexed to a clear blue solution to which was added about 0.76 mmole of $Mg(OH)_2$ giving after sonication a clear solution which was rotary evaporated to near dryness under reduced pressure at 34 C and put under high vacuum over $P_2O_5$ to give a blue powder. Nutrient preparations containing, for example, 0.5 mg, 1 mg, or 2 mg of copper per dose or serving of this material would also add about 1.1 mg, 2.1 mg, and 4.3 mg to the magnesium content due to other ingredients, respectively, and would also add about 0.031 mmoles, 0.063 mmoles, and 0.126 mmoles of 1,1,1-triaspartate, respectively. The triaspartate content per dose or serving can be further increased without changing the copper content by incorporation of triaspartic acid or other non-copper containing salts of triaspartic acid, for example magnesium triaspartate, calcium triaspartate and/or ferrous triaspartate.

Example G $Cupric_{1/4}$-$Mg_{1/4}$-1,1,1-triaspartate on microcrystalline cellulose: $Cupric_{1/4}$-$Mg_{1/4}$-1,1,1-triaspartate from Example F was put into 2 ml of water with sonication to give a dark blue solution, and an equal weight of USP grade microcrystalline cellulose added. After rotary evaporation to near dryness under reduced pressure at 37 C and exposure to high vacuum over $P_2O_5$ gave a light blue free flowing powder. This material can be added to nutrient preparation as in Example F, but using twice the weight to give the same amount of copper, magnesium, and triaspartate.

Example H $Cupric_{1/4}$-$Ca_{1/4}$-1,1,1-triaspartate: This was made in manner similar to Example F, but using $Ca(OH)_2$ instead of $Mg(OH)_2$.

Example I Cupric-Ca-1,1,1-triaspartate on microcrystalline cellulose: This was made in manner similar to Example G, but using Cupric-Ca-1,1,1-triaspartate instead of Cupric-Mg-1,1,1-triaspartate.

Example J $Cupric_{2.2}$-1,1,1-triaspartate: Cupric sulfate·$5H_2O$ (0.15 g, 0.60 mmoles) was dissolved in 1.0 ml water and 1M sodium carbonate added to give pH 9.1, the mixture centrifuged, and the supernate decanted and discarded. The precipitate was resuspended in 0.5 ml ice-cold water, centrifuged again, and the second supernate discarded. To this was added 0.27 mmoles of 1,1,1-triaspartic free acid as a 60 mM aqueous solution, vortexed to a clear blue solution, rotary evaporated to near dryness under reduced pressure at 38 C, and put under high vacuum over $P_2O_5$ to give blue flakes. On being left open to the atmosphere this material gained 11% weight over the following week, but remained free flowing. Nutrient preparations containing, for example, 0.5 mg, 1 mg, or 2 mg of copper per dose or serving of this material would also add about 0.0036 mmoles, 0.0072 mmoles, and 0.014 mmoles of 1,1,1-triaspartate, respectively. The triaspartate content per dose or serving can be further increased without changing the copper content by incorporation of triaspartic acid or other non-copper containing salts of triaspartic acid, for example magnesium triaspartate, calcium triaspartate and/or ferrous triaspartate.

Example K $Cupric_{1.1}$-1,1,1-triaspartate. All of the $cupric_{2.2}$-1,1,1-triaspartate from Example I was put back into solution and another 0.27 mmoles of 1,1,1-triaspartic free acid added, vortexed to a clear blue solution, rotary evaporated to near dryness under reduced pressure at 38 C, and put under high vacuum over $P_2O_5$ to give blue-green flakes that were free flowing and initially not sticky. Let open to the atmosphere (~50% relative humidity) this gained 6% in weight over 3 days and became slightly sticky. On exposure to 70 to 80% RH for another 24 hours weight gain increased to a total 10% and the material was wet and sticky.

Example L Cupric$_{1.1}$-1,1,1-triaspartate on microcrystalline cellulose. All of the cupric$_{1.1}$-1,1,1-triaspartate from example F was to put into solution by addition of 1.0 ml of water. USP grade microcrystalline cellulose was added in an amount equal to half the initial dry weight of the cupric$_{1.1}$-1,1,1-triaspartate, sonicated briefly to distribute, rotary evaporated to near dryness under reduced pressure, and put under high vacuum over $P_2O_5$ to give blue flakes. This material on exposure to 70% RH for a day and then 90% RH for an additional day gained about 10% in weight, but did not become sticky. Nutrient preparations containing, for example, 0.5 mg, 1 mg, or 2 mg of copper per dose or serving of this material would also add about 0.0072 mmoles, 0.014 mmoles, and 0.029 mmoles of 1,1,1-triaspartate, respectively. The triaspartate content per dose or serving can be further increased without changing the copper content by incorporation of triaspartic acid or other non-copper containing salts of triaspartic acid, for example magnesium triaspartate, calcium triaspartate and/or ferrous triaspartate.

Example M Cupric$_{3.1}$-1,1,1-triaspartate: Cupric sulfate·5H$_2$O (0.137 g, 0.55 mmoles) was dissolved in 1.0 ml water and 1M sodium carbonate added to give pH 9.1, the mixture centrifuged, and the supernate decanted and discarded. The precipitate was resuspended in 0.5 ml ice-cold water, recentrifuged, and the second supernate discarded. This was again resuspended in 0.5 ml water and 0.172 mmoles of 1,1,1-triaspartic free acid as a 60 mM aqueous solution added rapidly with vigorous vortexing and sonication. Unlike cupric-triaspartate made with a lower molar ratio of copper to peptide, unexpectedly a dark blue suspension was produced. This was centrifuged and dried under high vacuum over $P_2O_5$. On re-exposure to air this gained 11% in weight from uptake of water. Although this material is eventually soluble in water to the extent of about 2.8 g/L at 37° C., its dissolution is surprisingly slow. Cupric peptides with slow dissolution can be especially useful for inclusion in food or multivitamin-mineral preparations.

Example N Choline-1,1,1-triaspartate. To 5.0 ml of an aqueous 60 mM solution of 1,1,1-triaspartic free acid was added 0.77 ml of 20% choline in water (1.3 mmoles) to give a solution of pH 5.1. This was rotary evaporated to near dryness under reduced pressure, and put under high vacuum over $P_2O_5$ to give an off white powder. On exposure to ~50% RH, this material became a thick oil in less than 24 hours.

Example O Choline-1,1,1-triaspartate on microcrystalline cellulose. To all of the oily choline-1,1,1-triaspartate from Example M was added 1 ml water, mixed, a weight of USP grade microcrystalline cellulose was added in an amount equal to twice the initial dry weight of the choline-1,1,1-triaspartate, and sonicated. This was rotary evaporated to near dryness under reduced pressure at 37 C, and put under high vacuum over $P_2O_5$ to give an off white powder. Although this material gained weight on exposure to the atmosphere, it remained free flowing and not sticky for several months and even after 24 hours at 90% RH.

Example P Ferrous 1,1,1-triaspartate. To 133 mg of fresh iron(II) chloride 4H$_2$O was added 3 ml of well argon sparged water, mixed with further argon bubbling, and 1.3 ml of argon sparged 1 M NaOH added to produce a light green precipitate which was quickly centrifuged. After decanting the supernatant, well argon sparged 60 mM 1,1,1-triaspartic free acid was added and briefly sonicated under argon to give a light orange solution of pH 5.4, which was rotary evaporated at 26 C to near dryness under reduced pressure, and put under high vacuum over $P_2O_5$ to give light orange brown flakes. When kept open to the atmosphere this material gained 13% in weight over several days and became dark brown due to partial oxidation to iron(III). However, material open to air via a drying tube did not change color or significantly oxidize and was still soluble in water.

Example Q A multivitamin-mineral supplement containing 0.125 mmole triaspartate (56 mg of tetrasodium triaspartate on 56 mg of microcrystalline cellulose), 2 mg of copper (as cupric sulfate), 18 mg of iron (as ferrous fumerate), calcium carbonate (300 mg as elemental calcium), caffeine, magnesium oxide, ascorbic acid, guarana seed powder, crospovidone, beta-carotene, biotin, cholecalciferol, chromium chloride, croscarmellose sodium, cyanocobalamin, d-calcium pantothenate, dl-alpha-tocopheryl acetate, fd&c blue #1 lake, fd&c red #40 lake, fd&c yellow #5 (tartrazine) lake, folic acid, hydroxypropyl methylcellulose, manganese sulfate, niacinamide, phytonadione, polyethylene glycol, pyridoxine hydrochloride, riboflavin, silicon dioxide, sodium selenite, stearic acid, thiamine mononitrate, titanium dioxide, vitamin a acetate, zinc oxide.

It should be understood that the range of compositions is not limited by this particular list. Each of the nutrients can be present in a wide range of forms (for example vitamin B12 as cyanocobalamin or methylcobalamin or adenosylcobalamin), and in a wide range of weights (for example, vitamin B12 from less than 1 microgram or to more than 5 mg) as is common in the art of vitamin formulation. Nutrients can be omitted from the list, or further components added. The nature of the excipients is not to be constrained by the above list.

Example R A multivitamin-mineral supplement as in example Q but containing 0.125 mmole triaspartate (45 mg of triaspartic free acid) plus additional calcium carbonate to bring the pH closer to neutral on dissolution (about 25 mg, =10 mg of elemental calcium).

Example S A hair shampoo containing water, sodium lauryl sulfate, sodium laureth sulfate, cocamidopropyl betaine, sodium citrate, sodium xylenesulfonate, fragrance, sodium chloride, citric acid, sodium benzoate, hydroxypropyl methylcellulose, panthenol, panthenyl ethyl ether, methylchloroisothiazolinone, methylisothiazolinone and tetra-sodium-1,1,1-triaspartate in a concentration of about 1.1 mM (~0.05% w/w).

Example T A hair conditioner containing water, cetyl alcohol, stearamidopropyl dimethylamine, stearyl alcohol, quaternium-18, fragrance, bis-aminopropyl dimethicone, benzyl alcohol, cetearyl alcohol, hydroxypropyl guar, glyceryl stearate, citric acid, polysorbate 60, panthenol, panthenyl ethyl ether, oleyl alcohol, methylchloroisothiazolinone, methylisothiazolinone and tetra-sodium-1,1,1-triaspartate in a concentration of about 0.05% w/w.

Example U Garbanzos beans (chick peas) containing chick peas, water, salt, and a mixture of potassium diaspartate, triaspartate, and tetraaspartate, where the total concentration of three peptides is 0.3 mM, and triaspartate is the predominant peptide.

Example V A hematinic formulation containing 110 mg iron as ferrous fumarate (611% of the U.S. Daily Value for iron), 60 mg vitamin C as ascorbic acid (100% DV), microcrystalline cellulose, magnesium stearate, calcium phosphate, and 100 mg of a mixture of Asp-Asp, Asp-Asp-Asp, Asp-Asp-Asp-Asp [SEQ ID NO: 1] as a neutralized potassium salt (where Asp-Asp-Asp constitutes >50 mol % of the total).

We claim:

1. A composition comprising:
   a) an effective amount of one or more peptides, or a pharmaceutically acceptable salt thereof, wherein each of the one or more peptides consist of two to five amino acid residues, at least two of the residues are aspartic acid, and the one or more peptides do not contain histidine, wherein the effective amount of the one or more peptides is from 0.02 mM to 6 mM;
   b) a food product, a cosmetic product, or a hair care product, and
   c) a physiologically acceptable mineral capable of degrading the food product, the cosmetic product, or the hair care product; wherein the physiologically acceptable mineral is intentionally added to the composition or is endogenously present in the composition, wherein the physiologically acceptable mineral is copper, iron, chromium, zinc, manganese, or a combination of the foregoing; and
   wherein the effective amount of the one or more peptides slows metal catalyzed oxidative degradation of the food product, the cosmetic product, or the hair care product.

2. The composition of claim 1, wherein the effective amount of the one or more peptides decreases the rate of degradation of the food product, the cosmetic product, or the hair care product by at least 5%.

3. The composition of claim 1, wherein the pharmaceutically acceptable salt is a sodium salt, a potassium salt, a magnesium salt, a calcium salt, a choline salt, or a mixture of any two or more of the foregoing.

4. The composition of claim 1, wherein the food product, the cosmetic product or the hair care product is a cosmetic product or a hair product; and wherein the cosmetic product or the hair product is selected from the group consisting of a bath soap, a bath detergent, a moisturizing preparation, a deodorant, a cream, a lotion, a shampoo, a makeup product, a lipstick, and a sunscreen.

5. The composition of claim 1, wherein the one or more peptides is a sequence selected from the group consisting of: Asp-Asp-Asp, and SEQ ID NO: 3.

6. A method for decreasing the rate of decomposition of a food product, a cosmetic product, or a hair care product comprising incorporating into the food product, the cosmetic product, or the hair care product, an effective amount of one or more peptides, or a pharmaceutically acceptable salt thereof, and a physiologically acceptable mineral capable of degrading the food product, the cosmetic product, or the hair care product,
   wherein each of the one or more peptides consist of two to five amino acid residues, at least two of the residues are aspartic acid, and the one or more peptides do not contain histidine, wherein the effective amount of the one or more peptides is from 0.02 mM to 6 mM;

wherein the physiologically acceptable mineral is intentionally added to the food product, the cosmetic product, or the hair care product or is endogenously present in the food product, the cosmetic product, or the hair care product, wherein the physiologically acceptable mineral is copper, iron, chromium, zinc, manganese, or a combination of the foregoing; and wherein the effective amount of the one or more peptides slows metal catalyzed oxidative degradation of the food product, the cosmetic product, or the hair care product.

7. The method of claim 6, wherein the effective amount of the one or more peptides decreases the rate of degradation of the food product, the cosmetic product, or the hair care product by at least 5%.

8. The method of claim 6, wherein the pharmaceutically acceptable salt is a sodium salt, a potassium salt, an iron salt, a magnesium salt, a calcium salt, a copper salt, a choline salt, or a mixture of any two or more of the foregoing.

9. The method of claim 6, wherein the one or more peptides is a sequence selected from the group consisting of: Asp-Asp, Asp-Asp-Asp, SEQ ID NO: 1, Ala-Asp-Asp, Asp-Asp-Glu, SEQ ID NO: 3, Glu-Asp-Asp, and SEQ ID NO: 15.

10. The composition of claim 1, wherein the one or more peptides have a free N-terminal amino group.

11. The composition of claim 1, wherein the one or more peptides are selected from the group consisting of: Asp-Asp, Asp-Asp-Cys, Asp-Asp-Met, Asp-Glu-Asp, Arg-Asp-Asp, Lys-Asp-Asp, Asp-Asp-Ala, Asp-Asp-Glu, Asp-Asp-Ala, Gly-Asp-Asp, Ala-Asp-Asp, Val-Asp-Asp, Leu-Asp-Asp, Phe-Asp-Asp, Tyr-Asp-Asp, Asp-Asp-Try, Asp-Asp-Phe, Ala-Asp-Asp, SEQ ID NO: 1, SEQ ID NO: 2, SEQ ID NO: 14, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO: 11, SEQ ID NO: 12, and SEQ ID NO: 13.

12. A composition comprising:
a) an effective amount of one or more peptides, or a pharmaceutically acceptable salt thereof, wherein each of the one or more peptides consist of two to five amino acid residues, at least two of the residues are aspartic acid, and the one or more peptides do not contain histidine, wherein the effective amount of the one or more peptides is from 0.01 mmol to 3.0 mmol per serving size of the composition;
a) a vitamin and mineral supplement product; and
c) a physiologically acceptable mineral capable of degrading the vitamin and mineral supplement product; wherein the physiologically acceptable mineral is intentionally added to the composition or is endogenously present in the composition; wherein the physiologically acceptable mineral is copper, iron, chromium, zinc, manganese, or a combination of the foregoing;
wherein the effective amount of the one or more peptides slows the metal catalyzed oxidative decomposition of the vitamin and mineral supplement product; and
wherein the one or more peptides have both free amino and free carboxy terminals.

13. The composition of claim 12, wherein the effective amount of the one or more peptides decreases the rate of degradation of the vitamin and mineral supplement product by at least 5%.

14. The composition of claim 12, wherein the pharmaceutically acceptable salt is a sodium salt, a potassium salt, a magnesium salt, a calcium salt, a choline salt, or a mixture of any two or more of the foregoing.

15. The composition of claim 12, wherein the composition is a powder, a tablet, a capsule, a caplet, a gummy, a chew, an effervescent, a lozenge, a confectionery, a solution, a syrup, or a suspension.

16. The composition of claim 12, wherein the one or more peptides is a sequence selected from the group consisting of: Asp-Asp-Asp, and SEQ ID NO: 3.

17. The composition of claim 12, wherein the one or more peptides are selected from the group consisting of: Asp-Asp, Asp-Asp-Cys, Asp-Asp-Met, Asp-Glu-Asp, Arg-Asp-Asp, Lys-Asp-Asp, Asp-Asp-Ala, Asp-Asp-Glu, Asp-Asp-Ala, Gly-Asp-Asp, Ala-Asp-Asp, Val-Asp-Asp, Leu-Asp-Asp, Phe-Asp-Asp, Tyr-Asp-Asp, Asp-Asp-Try, Asp-Asp-Phe, Ala-Asp-Asp, SEQ ID NO: 1, SEQ ID NO: 2, SEQ ID NO: 14, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO: 11, SEQ ID NO: 12, and SEQ ID NO: 13.

18. The composition of claim 1, wherein the one or more peptides consist of two aspartic acid residues, and any combination of one to three amino acids selected from the group consisting of: glutamic acid, glycine, alanine, valine, leucine, isoleucine, serine, cysteine, selenocysteine, threonine, methionine, proline, phenylalanine, tyrosine, tryptophan, lysine, arginine, asparagine, glutamine, phosphoserine, phosphothreonine, phosphotyrosine, phosphoaspartic acid, phosphoglutamic acid, phosphocysteine, gamma-carboxy-glutamate, pyrrolysine, selenocysteine, hydroxylated asparagine, hydroxylated aspartic acid, hydroxylated proline, hydroxylated lysine, methyl lysine, methyl glutamic acid, sulfonated serine, sulfonated threonine, sulfonated tyrosine, and citrulline.

19. The composition of claim 12, wherein the one or more peptides consist of two aspartic acid residues, and any combination of one to three amino acids selected from the group consisting of: glutamic acid, glycine, alanine, valine, leucine, isoleucine, serine, cysteine, selenocysteine, threonine, methionine, proline, phenylalanine, tyrosine, tryptophan, lysine, arginine, asparagine, glutamine, phosphoserine, phosphothreonine, phosphotyrosine, phosphoaspartic acid, phosphoglutamic acid, phosphocysteine, gamma-carboxy-glutamate, pyrrolysine, selenocysteine, hydroxylated asparagine, hydroxylated aspartic acid, hydroxylated proline, hydroxylated lysine, methyl lysine, methyl glutamic acid, sulfonated serine, sulfonated threonine, sulfonated tyrosine, and citrulline.

20. A method for decreasing the rate of decomposition of a vitamin and mineral supplement product, comprising incorporating into the vitamin and mineral supplement product an effective amount of one or more peptides, or a pharmaceutically acceptable salt thereof, and a physiologically acceptable mineral capable of degrading the vitamin and mineral supplement product,
wherein each of the one or more peptides consist of two to five amino acid residues, at least two of the residues are aspartic acid, and the one or more peptides do not contain histidine, wherein the effective amount of the one or more peptides is from 0.01 mmol to 3.0 mmol per serving size of the vitamin and mineral supplement product;
wherein the physiologically acceptable mineral is intentionally added to the vitamin and mineral supplement product or is endogenously present in the vitamin and mineral supplement product;
wherein the physiologically acceptable mineral is copper, iron, chromium, zinc, manganese, or a combination of the foregoing;

wherein the effective amount of the one or more peptides slows the metal catalyzed oxidative decomposition of the vitamin and mineral supplement product; and wherein the one or more peptides have both free amino and free carboxy terminals.

* * * * *

SEQUENCE LISTING

<160> NUMBER OF SEQ ID NOS: 15

<210> SEQ ID NO 1
<211> LENGTH: 4
<212> TYPE: PRT
<213> ORGANISM: Artificial Sequence
<220> FEATURE:
<223> OTHER INFORMATION: Synthesised Sequence

<400> SEQUENCE: 1

Asp Asp Asp Asp
1

<210> SEQ ID NO 2
<211> LENGTH: 5
<212> TYPE: PRT
<213> ORGANISM: Artificial Sequence
<220> FEATURE:
<223> OTHER INFORMATION: Synthesised Sequence

<400> SEQUENCE: 2

Asp Asp Asp Asp Asp
1               5

<210> SEQ ID NO 3
<211> LENGTH: 4
<212> TYPE: PRT
<213> ORGANISM: Artificial Sequence
<220> FEATURE:
<223> OTHER INFORMATION: Synthesised Sequence

<400> SEQUENCE: 3

Asp Asp Asp Glu
1

<210> SEQ ID NO 4
<211> LENGTH: 4
<212> TYPE: PRT
<213> ORGANISM: Artificial Sequence
<220> FEATURE:
<223> OTHER INFORMATION: Synthesised Sequence

<400> SEQUENCE: 4

Ala Asp Asp Asp
1

<210> SEQ ID NO 5
<211> LENGTH: 4
<212> TYPE: PRT
<213> ORGANISM: Artificial Sequence
<220> FEATURE:
<223> OTHER INFORMATION: Synthesised Sequence

<400> SEQUENCE: 5

Gly Asp Asp Asp
1

<210> SEQ ID NO 6
<211> LENGTH: 4
<212> TYPE: PRT
<213> ORGANISM: Artificial Sequence
<220> FEATURE:
<223> OTHER INFORMATION: Synthesised Sequence

<400> SEQUENCE: 6

Arg Asp Asp Asp
1

```
<210> SEQ ID NO 7
<211> LENGTH: 4
<212> TYPE: PRT
<213> ORGANISM: Artificial Sequence
<220> FEATURE:
<223> OTHER INFORMATION: Synthesised Sequence

<400> SEQUENCE: 7

Lys Asp Asp Asp
1

<210> SEQ ID NO 8
<211> LENGTH: 4
<212> TYPE: PRT
<213> ORGANISM: Artificial Sequence
<220> FEATURE:
<223> OTHER INFORMATION: Synthesised Sequence

<400> SEQUENCE: 8

Arg Asp Asp Arg
1

<210> SEQ ID NO 9
<211> LENGTH: 4
<212> TYPE: PRT
<213> ORGANISM: Artificial Sequence
<220> FEATURE:
<223> OTHER INFORMATION: Synthesised Sequence

<400> SEQUENCE: 9

Arg Asp Asp Lys
1

<210> SEQ ID NO 10
<211> LENGTH: 4
<212> TYPE: PRT
<213> ORGANISM: Artificial Sequence
<220> FEATURE:
<223> OTHER INFORMATION: Synthesised Sequence

<400> SEQUENCE: 10

Arg Asp Asp Asn
1

<210> SEQ ID NO 11
<211> LENGTH: 4
<212> TYPE: PRT
<213> ORGANISM: Artificial Sequence
<220> FEATURE:
<223> OTHER INFORMATION: Synthesised Sequence

<400> SEQUENCE: 11

Arg Asp Asp Phe
1

<210> SEQ ID NO 12
<211> LENGTH: 4
<212> TYPE: PRT
<213> ORGANISM: Artificial Sequence
<220> FEATURE:
<223> OTHER INFORMATION: Synthesised Sequence

<400> SEQUENCE: 12

Arg Asp Asp Leu
1
```

```
<210> SEQ ID NO 13
<211> LENGTH: 4
<212> TYPE: PRT
<213> ORGANISM: Artificial Sequence
<220> FEATURE:
<223> OTHER INFORMATION: Synthesised Sequence

<400> SEQUENCE: 13

Arg Asp Asp Val
1

<210> SEQ ID NO 14
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: X is beta
<220> FEATURE:
<221> NAME/KEY: misc_feature
<222> LOCATION: (4)..(4)
<223> OTHER INFORMATION: Xaa can be any naturally occurring amino acid

<400> SEQUENCE: 14

Asp Asp Asp Xaa Asp
1               5

<210> SEQ ID NO 15
<211> LENGTH: 4
<212> TYPE: PRT
<213> ORGANISM: Artificial sequence
<220> FEATURE:
<223> OTHER INFORMATION: Synthetic construct

<400> SEQUENCE: 15

Glu Asp Asp Asp
1
```